US010064945B2

(12) United States Patent
Barnscheid et al.

(10) Patent No.: US 10,064,945 B2
(45) Date of Patent: Sep. 4, 2018

(54) THERMOFORMED, TAMPER-RESISTANT PHARMACEUTICAL DOSAGE FORM CONTAINING ZINC

(71) Applicant: GRÜNENTHAL GMBH, Aachen (DE)

(72) Inventors: Lutz Barnscheid, Mönchengladach (DE); Eric Galia, Aachen (DE); Anja Geißler, Stolberg (DE); Jana Pätz, Bonn (DE); Sebastian Schwier, Aachen (DE); Julia Baronsky-Probst, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 13/891,306

(22) Filed: May 10, 2013

(65) Prior Publication Data
US 2013/0303623 A1 Nov. 14, 2013

Related U.S. Application Data

(60) Provisional application No. 61/645,659, filed on May 11, 2012.

(30) Foreign Application Priority Data

May 11, 2012 (EP) .................................. 12003743

(51) Int. Cl.
A61K 47/10 (2017.01)
A61K 31/137 (2006.01)
A61K 9/20 (2006.01)

(52) U.S. Cl.
CPC ............ A61K 47/10 (2013.01); A61K 9/2031 (2013.01); A61K 9/2054 (2013.01); A61K 31/137 (2013.01)

(58) Field of Classification Search
CPC ..................................................... A61K 47/10
See application file for complete search history.

(56) References Cited

U.S. PATENT DOCUMENTS

| 2,524,855 | A | | 10/1950 | Schnider et al. |
| 2,806,033 | A | | 9/1957 | Lewenstein et al. |
| 2,987,445 | A | | 6/1961 | Levesque |
| 3,332,950 | A | | 7/1967 | Blumberg et al. |
| 3,370,035 | A | * | 2/1968 | Ogura ............ C08K 5/39 524/106 |
| 3,652,589 | A | | 3/1972 | Flick et al. |
| 3,806,603 | A | | 4/1974 | Gaunt et al. |
| 3,865,108 | A | | 2/1975 | Hartop |
| 3,941,865 | A | | 3/1976 | Miller et al. |
| 3,966,747 | A | | 6/1976 | Monkovic et al. |
| 3,980,766 | A | | 9/1976 | Shaw et al. |
| 4,002,173 | A | | 1/1977 | Manning et al. |
| 4,014,965 | A | | 3/1977 | Stube et al. |
| 4,070,494 | A | | 1/1978 | Hoffmeister et al. |
| 4,070,497 | A | | 1/1978 | Wismer et al. |
| 4,175,119 | A | | 11/1979 | Porter |
| 4,200,704 | A | | 4/1980 | Stanley et al. |
| 4,207,893 | A | | 6/1980 | Michaels |
| 4,262,017 | A | | 4/1981 | Kuipers et al. |
| 4,343,789 | A | | 8/1982 | Kawata et al. |
| 4,353,887 | A | | 10/1982 | Hess et al. |
| 4,404,183 | A | | 9/1983 | Kawata et al. |
| 4,427,681 | A | | 1/1984 | Munshi et al. |
| 4,427,778 | A | | 1/1984 | Zabriskie |
| 4,457,933 | A | | 7/1984 | Gordon et al. |
| 4,462,941 | A | | 7/1984 | Lee et al. |
| 4,473,640 | A | | 9/1984 | Combie et al. |
| 4,483,847 | A | | 11/1984 | Augart |
| 4,485,211 | A | | 11/1984 | Okamoto |
| 4,529,583 | A | | 7/1985 | Porter |
| 4,599,342 | A | | 7/1986 | La Hann |
| 4,603,143 | A | | 7/1986 | Schmidt |
| 4,612,008 | A | | 9/1986 | Wong et al. |
| 4,629,621 | A | | 12/1986 | Snipes |
| 4,667,013 | A | | 5/1987 | Reichle |
| 4,690,822 | A | | 9/1987 | Uemura |
| 4,713,243 | A | | 12/1987 | Schiraldi et al. |
| 4,744,976 | A | | 5/1988 | Snipes et al. |
| 4,764,378 | A | | 8/1988 | Keitn et al. |
| 4,765,989 | A | | 8/1988 | Wong et al. |
| 4,774,074 | A | | 9/1988 | Snipes |
| 4,774,092 | A | | 9/1988 | Hamilton |
| 4,783,337 | A | | 11/1988 | Wong et al. |
| 4,806,337 | A | | 2/1989 | Snipes et al. |
| RE33,093 | E | | 10/1989 | Schiraldi et al. |
| 4,880,585 | A | | 11/1989 | Klimesch et al. |

(Continued)

FOREIGN PATENT DOCUMENTS

AR  046994 A1  12/2004
AR  045353 A1  10/2005

(Continued)

OTHER PUBLICATIONS

Mises à jour cumulatives, Vidal, Jan./Oct. 2002.

(Continued)

Primary Examiner — Andrew S Rosenthal
(74) Attorney, Agent, or Firm — Norris McLaughlin & Marcus, P.A.

(57) ABSTRACT

A thermoformed, tamper-resistant pharmaceutical dosage form comprises:
a) a pharmacologically active ingredient;
b) a polyalkylene oxide having a weight average molecular weight of more than 200,000 g/mol; and
c) a zinc component, wherein the content of said zinc component is at least 1 ppm, relative to the total weight of the pharmaceutical dosage form.

When the pharmacologically active ingredient is effective against pain, the pharmaceutical dosage form may be used in a method of treating pain. When the pharmacologically active ingredient has abuse potential, the pharmaceutical dosage form may be used in a method of reducing the incidence of the abuse of said pharmacologically active ingredient.

28 Claims, No Drawings

(56) References Cited

U.S. PATENT DOCUMENTS

| | | |
|---|---|---|
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen et al. |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake et al. |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 6/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Lancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |

(56) References Cited

U.S. PATENT DOCUMENTS

| | | |
|---|---|---|
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Mari et al. |
| 8,858,963 B1 | 10/2014 | Devarakonda et al. |
| 8,901,113 B2 | 12/2014 | Leech et al. |
| 9,192,578 B2 | 11/2015 | McGinity et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0215508 A1 | 1/2003 | Davis et al. |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler et al. |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1* | 2/2005 | Bartholomaus ...... A61K 9/2031 424/10.1 |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1* | 1/2006 | Bartholomaus ...... A61K 9/2027 424/10.1 |
| 2006/0004034 A1 | 1/2006 | Hinze et al. |
| 2006/0009478 A1 | 1/2006 | Friedman et al. |
| 2006/0012701 A1 | 1/2006 | Sung-Bin |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaeus et al. |
| 2006/0193914 A1 | 8/2006 | Ashworth |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Midon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |

(56) References Cited

U.S. PATENT DOCUMENTS

| | | |
|---|---|---|
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1* | 9/2010 | Babul .................... 514/21.4 |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0028972 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaus et al. |
| 2016/0184297 A1 | 6/2016 | Aeikffnau-Maric et al. |
| 2016/0256456 A1 | 9/2016 | Caruso et al. |
| 2016/0263037 A1 | 9/2016 | Arkenau Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaus et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006/210145 B2 | 8/2006 |
| AU | 2006210145 A1 | 8/2006 |
| AU | 2009207796 A1 | 7/2009 |
| AU | 2009243681 A1 | 11/2009 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2594713 A1 | 6/2006 |
| CA | 2595954 A1 | 7/2006 |
| CA | 2229650 C | 8/2006 |
| CA | 2595979 A1 | 8/2006 |

(56) References Cited

FOREIGN PATENT DOCUMENTS

| | | |
|---|---|---|
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 10036400 A1 | 6/2002 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004020220 A1 | 10/2005 |
| DE | 102004019916 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0864326 A2 | 9/1919 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 | | |
| EP | 0226061 A2 | 6/1987 | | |
| EP | 0228417 A1 | 7/1987 | | |
| EP | 0229652 A2 | 7/1987 | | |
| EP | 0232877 A2 | 8/1987 | | |
| EP | 0239973 A2 | 10/1987 | | |
| EP | 0239973 A2 * | 10/1987 | ............. | C08G 65/12 |
| EP | 0240906 A2 | 10/1987 | | |
| EP | 0261616 A2 | 3/1988 | | |
| EP | 0261616 A3 | 3/1988 | | |
| EP | 0270954 A1 | 6/1988 | | |
| EP | 0277289 A1 | 8/1988 | | |
| EP | 0293066 A2 | 11/1988 | | |
| EP | 0328775 A1 | 8/1989 | | |
| EP | 0228417 B1 | 8/1990 | | |
| EP | 0229652 B1 | 10/1991 | | |
| EP | 0477135 A1 | 3/1992 | | |
| EP | 0277289 B1 | 4/1992 | | |
| EP | 0293066 B1 | 4/1993 | | |
| EP | 0270954 B1 | 5/1993 | | |
| EP | 0544144 A1 | 6/1993 | | |
| EP | 0583726 A2 | 2/1994 | | |
| EP | 0598606 A1 | 5/1994 | | |
| EP | 0641195 A1 | 3/1995 | | |
| EP | 0647448 A1 | 4/1995 | | |
| EP | 0654263 A1 | 5/1995 | | |
| EP | 0661045 A1 | 7/1995 | | |
| EP | 0675710 A1 | 10/1995 | | |
| EP | 0682945 A2 | 11/1995 | | |
| EP | 0636370 A1 | 12/1995 | | |
| EP | 0693475 A1 | 1/1996 | | |
| EP | 0820693 A1 | 1/1996 | | |
| EP | 0696598 A1 | 2/1996 | | |
| EP | 0216453 B1 | 3/1996 | | |
| EP | 0583726 B1 | 11/1996 | | |
| EP | 0756480 A1 | 2/1997 | | |
| EP | 0760654 A1 | 3/1997 | | |
| EP | 0780369 A1 | 6/1997 | | |
| EP | 0785775 A1 | 7/1997 | | |
| EP | 0761211 A1 | 12/1997 | | |
| EP | 0809488 A1 | 12/1997 | | |
| EP | 0820698 A1 | 1/1998 | | |
| EP | 0820753 A2 | 1/1998 | | |
| EP | 0857062 A2 | 8/1998 | | |
| EP | 0864324 A1 | 9/1998 | | |
| EP | 0598606 B1 | 6/1999 | | |
| EP | 0675710 B1 | 8/1999 | | |
| EP | 0980894 A1 | 2/2000 | | |
| EP | 0988106 A1 | 3/2000 | | |
| EP | 1014941 A1 | 7/2000 | | |
| EP | 1070504 A1 | 1/2001 | | |
| EP | 1127871 A1 | 8/2001 | | |
| EP | 1138321 A2 | 10/2001 | | |
| EP | 1152026 A1 | 11/2001 | | |
| EP | 1138321 A3 | 1/2002 | | |
| EP | 1166776 A2 | 1/2002 | | |
| EP | 1201233 A1 | 5/2002 | | |
| EP | 0661045 B1 | 7/2002 | | |
| EP | 1250045 | 10/2002 | | |
| EP | 1250045 A2 | 10/2002 | | |
| EP | 1251120 A1 | 10/2002 | | |
| EP | 1293127 A2 | 3/2003 | | |
| EP | 1293195 A1 | 3/2003 | | |
| EP | 1293196 A2 | 3/2003 | | |
| EP | 1127871 B1 | 9/2003 | | |
| EP | 1201233 B1 | 12/2004 | | |
| EP | 1251120 B1 | 12/2004 | | |
| EP | 1492506 B1 | 1/2005 | | |
| EP | 1166776 B1 | 2/2005 | | |
| EP | 1502592 A1 | 2/2005 | | |
| EP | 1658054 A1 | 2/2005 | | |
| EP | 1658055 A1 | 2/2005 | | |
| EP | 1515702 B1 | 3/2005 | | |
| EP | 1527775 A1 | 4/2005 | | |
| EP | 1558221 A1 | 8/2005 | | |
| EP | 1558257 A1 | 8/2005 | | |
| EP | 1560585 B1 | 8/2005 | | |
| EP | 1611880 A2 | 1/2006 | | |
| EP | 1658054 B1 | 5/2006 | | |

(56) References Cited

FOREIGN PATENT DOCUMENTS

| | | | |
|---|---|---|---|
| EP | 1138321 B1 | 1/2007 | |
| EP | 1740161 A2 | 1/2007 | |
| EP | 1658055 B1 | 3/2007 | |
| EP | 1765303 A1 | 3/2007 | |
| EP | 1786403 A1 | 5/2007 | |
| EP | 1558221 B1 | 6/2007 | |
| EP | 1842533 A2 | 10/2007 | |
| EP | 1845955 A1 | 10/2007 | |
| EP | 1845956 A1 | 10/2007 | |
| EP | 1859789 A1 | 11/2007 | |
| EP | 1980245 A1 | 10/2008 | |
| EP | 1897545 A1 | 12/2008 | |
| EP | 2131830 A2 | 12/2009 | |
| EP | 2246063 A1 | 11/2010 | |
| EP | 2249811 A1 | 11/2010 | |
| EP | 2273983 A1 | 1/2011 | |
| EP | 2402004 A2 * | 1/2012 | ........... A61K 9/2009 |
| ES | 2336571 T3 | 12/2004 | |
| ES | 2260042 T3 | 11/2006 | |
| ES | 2285497 T3 | 11/2007 | |
| ES | 2288621 T3 | 1/2008 | |
| ES | 2289542 T3 | 2/2008 | |
| ES | 2315505 T3 | 4/2009 | |
| GB | 1147210 A | 4/1969 | |
| GB | 1567727 A | 5/1980 | |
| GB | 2047095 A | 11/1980 | |
| GB | 2057878 A | 4/1981 | |
| GB | 2238478 A | 6/1991 | |
| HR | 20070456 T3 | 6/2007 | |
| HR | 20070272 T3 | 11/2007 | |
| JP | S36-022895 | 11/1961 | |
| JP | S55162714 A | 12/1980 | |
| JP | S5659708 A | 5/1981 | |
| JP | S56169622 A | 12/1981 | |
| JP | S62240061 A | 10/1987 | |
| JP | H0249719 A | 2/1990 | |
| JP | 03-501737 A | 4/1991 | |
| JP | H0517566 A | 1/1993 | |
| JP | H06507645 A | 9/1994 | |
| JP | 08053331 A | 2/1996 | |
| JP | 8-505076 A | 6/1996 | |
| JP | H09508410 A | 8/1997 | |
| JP | H1057450 A | 3/1998 | |
| JP | H10251149 A | 9/1998 | |
| JP | 2002524150 A | 8/2002 | |
| JP | 2002-275175 A | 9/2002 | |
| JP | 2003125706 A | 5/2003 | |
| JP | 2003528598 A | 9/2003 | |
| JP | 2005506965 A | 3/2005 | |
| JP | 2005515152 A | 5/2005 | |
| JP | 2005534664 A | 11/2005 | |
| JP | 2007501201 A | 1/2007 | |
| JP | 2007501202 A | 1/2007 | |
| JP | 2007513147 A | 5/2007 | |
| JP | 2007533692 A | 11/2007 | |
| JP | 2008504327 A | 2/2008 | |
| JP | 2008024603 A | 7/2008 | |
| JP | 2008528654 A | 7/2008 | |
| JP | 2009523833 A | 6/2009 | |
| JP | 2009531453 A | 9/2009 | |
| JP | 2009537456 A | 10/2009 | |
| JP | 2011504455 A | 2/2011 | |
| JP | 2011506493 A | 3/2011 | |
| JP | 2013536810 A | 9/2013 | |
| JP | 2014505736 A | 3/2014 | |
| JP | 2014528437 A | 10/2014 | |
| KR | 1020060069832 A | 6/2006 | |
| KR | 20070039041 A | 4/2007 | |
| KR | 20070111510 A | 11/2007 | |
| KR | 20090085312 A | 8/2009 | |
| KR | 20100111303 A | 10/2010 | |
| KR | 20110016921 A | 2/2011 | |
| MX | 2007000008 A | 3/2007 | |
| MX | 2007000009 A | 3/2007 | |
| MX | 2007009393 A | 8/2007 | |
| MX | 201000818 A | 8/2010 | |
| MX | 2010012039 A | 11/2010 | |
| NO | 20061054 A | 3/2006 | |
| NO | 20070578 A | 1/2007 | |
| NO | 20074412 A | 11/2007 | |
| NZ | 528302 A | 2/2007 | |
| PT | 1699440 E | 12/2004 | |
| PT | 1658054 E | 5/2006 | |
| PT | 1658055 E | 7/2007 | |
| PT | 1515702 E | 12/2008 | |
| RU | 213 244 C1 | 6/1999 | |
| RU | 2198197 C2 | 2/2003 | |
| RU | 2220715 C2 | 1/2004 | |
| RU | 2328275 C2 | 5/2004 | |
| RU | 2396944 C2 | 7/2004 | |
| RU | 2326654 C2 | 9/2005 | |
| RU | 2339365 C2 | 12/2007 | |
| RU | 2354357 C2 | 12/2007 | |
| RU | 20071037 2 A | 9/2008 | |
| RU | 2007103707 A | 11/2008 | |
| RU | 2007132975 A | 4/2009 | |
| RU | 2567723 C2 | 11/2015 | |
| SI | 1515702 T1 | 4/2009 | |
| SI | 1699440 T1 | 11/2009 | |
| SK | 10612003 A3 | 1/2004 | |
| SU | 1759445 A1 | 9/1992 | |
| TW | I254634 B | 5/2006 | |
| WO | WO 1980/00841 A1 | 5/1980 | |
| WO | WO 1989/05624 A1 | 6/1989 | |
| WO | WO 1990/03776 A1 | 4/1990 | |
| WO | WO 1993/06723 A1 | 4/1993 | |
| WO | WO 93/10765 A1 | 6/1993 | |
| WO | WO 1993/10758 A1 | 6/1993 | |
| WO | WO 1993/11749 A1 | 6/1993 | |
| WO | WO 1993/23017 A1 | 11/1993 | |
| WO | WO 1994/06414 A1 | 3/1994 | |
| WO | WO 1994/08567 A1 | 4/1994 | |
| WO | WO 1995/17174 A1 | 6/1995 | |
| WO | WO 1995/20947 A1 | 8/1995 | |
| WO | WO 1995/22319 A1 | 8/1995 | |
| WO | WO 1995/30422 A1 | 11/1995 | |
| WO | WO 1996/00066 A1 | 1/1996 | |
| WO | WO 1996/03979 A1 | 2/1996 | |
| WO | WO 1996/14058 A1 | 5/1996 | |
| WO | WO 1997/000673 A1 | 1/1997 | |
| WO | WO 1997/33566 A2 | 9/1997 | |
| WO | WO 1997/49384 A1 | 12/1997 | |
| WO | WO 1998/35655 A3 | 2/1998 | |
| WO | WO 1998/20073 A2 | 5/1998 | |
| WO | WO 1998/28698 A1 | 7/1998 | |
| WO | WO 1998/35655 A2 | 8/1998 | |
| WO | WO 1998/051758 A1 | 11/1998 | |
| WO | WO 1999/12864 A1 | 3/1999 | |
| WO | WO 1999/32120 A1 | 7/1999 | |
| WO | WO 1999/44591 A1 | 9/1999 | |
| WO | WO 1999/045887 A2 | 9/1999 | |
| WO | WO 1999/48481 A1 | 9/1999 | |
| WO | WO 2000/0013647 A1 | 3/2000 | |
| WO | WO 2000/33835 A1 | 6/2000 | |
| WO | WO 2000/40205 A2 | 7/2000 | |
| WO | WO 2001/08661 A2 | 2/2001 | |
| WO | WO 2001/12230 A1 | 2/2001 | |
| WO | WO 2001/15667 A1 | 3/2001 | |
| WO | WO 2001/52651 A2 | 7/2001 | |
| WO | WO 2001/058451 A1 | 8/2001 | |
| WO | WO 2001/97783 A1 | 12/2001 | |
| WO | WO 2002/26061 A1 | 4/2002 | |
| WO | WO 2002/26262 A2 | 4/2002 | |
| WO | WO 2002/26928 A1 | 4/2002 | |
| WO | WO 2002/35991 A2 | 5/2002 | |
| WO | WO 2002/71860 A1 | 9/2002 | |
| WO | WO 2002/88217 A1 | 11/2002 | |
| WO | WO 2002/094254 A2 | 11/2002 | |
| WO | WO 2003/006723 A1 | 1/2003 | |
| WO | WO 2003/013433 A2 | 2/2003 | |
| WO | WO 2003/013476 A1 | 2/2003 | |
| WO | WO 2003/013479 A1 | 2/2003 | |
| WO | WO 2003/013538 A1 | 2/2003 | |
| WO | WO 2003/015531 A2 | 2/2003 | |

(56) References Cited

FOREIGN PATENT DOCUMENTS

| | | |
|---|---|---|
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A1 | 5/2003 |
| WO | WO 2003/039561 A1 | 5/2003 |
| WO | WO 2003/049689 A2 | 6/2003 |
| WO | WO 2003/053417 A1 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A1 | 4/2005 |
| WO | WO 2005/041968 A1 | 5/2005 |
| WO | WO 2005/053587 A1 | 6/2005 |
| WO | WO 2005/053656 A1 | 6/2005 |
| WO | WO 20051055981 A1 | 6/2005 |
| WO | WO 2005/060942 A1 | 7/2005 |
| WO | WO 2005/063214 A1 | 7/2005 |
| WO | WO 2005/065646 A1 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/0088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

PCT Second Written Opinion for PCT Application No. PCT/EP2013/053893 dated Feb. 21, 2014.
Carbopol 71G, retrieved Mar. 10, 2014 from http://www.lubrizol.com/LifeScience/Products/Carbopol71G-NF.html.
POLYOX WSR-303, retrieved Mar. 10, 2014 from URL http://www.dow.com/dowwolff/en/industrial_solutions/polymers/polyethylene.

(56) References Cited

OTHER PUBLICATIONS 2.9 Methoden der pharmazeutischen Technologie, European Pharmacopeia, 143-144, 1997. (Full English translation attached).
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J. Org Chem. 28(1), pp. 152-155, Abstract 1963.
Avis, Kenneth. Parenteral Preparations. Chapter 85. pp. 1518-1541In Remington's Pharmaceutical Sciences, 17th Ed, 1985.
Bailey, F.E., "Some properties of poly(ethylene oxide)' in aqueous solution," Journal of Applied Polymer Sciences, vol. 1, Issue No. 1, pp. 56-62, 1959.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al., "The impact of the addition of naloxone on the use and abuse of pentazocine", Public Health Reports, Jul.-Aug. 1987, vol. 102, No. 4, p. 426-429.
Block, Lawrence. Medicated Applications. Chapter 88. In Remington's Pharmaceutical Sciences, 17th Ed, 1985.
Braun, et al. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Cawello, "Parameters for Compartment-free Pharmacokinetics—Standardization of Study Design, Data Analysis and Reporting" 1999, pp. XI-XIII (table of contents).
Committe for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion", Pharmaceutical Technology, 62-70, Jan. 2005.
Cornish, P. "Avoid the Crush": hazards of medication administratien in patients with dysphagia or a feeding tube, CMA Media 5316., CMAJ. 172(7), pages 871-872. 2005.
Costa et al. "Modeling and comparison of dissolution profiles"; European Journal of Pharmaceutical Sciences 13 (2001) 123-33.
Crowley M.M. et al., Biomaterials 23, 2002, pp. 4241-4248.
Crowley MM,Drug Dev Ind Pharm. Sep. 2007;33(9):909-26.(Abstract only).
Dachille et al., "High-pressure Phase Transformations in Laboratory Mechanical Mixers and Mortars", Nature, vol. 186, Apr. 2, 1960, pp. 34 and 71.
Dachille. F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000.
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.

Dexheimer, Terahertz Spectroscopy: Principles and Applications (Optical Science and Engineering Series), CRC; 1 edition 2007. (Table of content only).
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolina, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolina, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolina, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolina, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolina, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolina, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83.pp. 1487-1491 in Remington's Pharmaceutical Sciences, 17th Ed, 1985.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion, Application No, 11006253-6-2112, dated Dec. 16, 2011.
European Search Report and Opinion, Application No. 11006254. 4-2112, dated Dec. 16, 2011.
European Search Report and Opinion, Application No. 11008131. 2-1219, dated Feb. 24, 2012.
European Search Report and Opinion, Application No. 11009129. 5-2112, dated Apr. 10, 2012.
European Search Report and Opinion, Application No. 12001301. 6-1219, dated Jun. 26, 2012.
European Search Report and Opinion, Application No. 12002708. 1-1219, dated Sep. 24, 2012.
European Search Report and Opinion, Application No. 12003743. 7-1219, dated Sep. 24, 2012.
European Search Report, Application No. 12001296.8-1219, dated Jun. 26, 2012.
Evonik Industries, Eudragit Application Guidelines, 10th Edition, 2008, (Table of Contents only).

(56) References Cited

OTHER PUBLICATIONS

Fell J.T., et al, "Determinination of Tablet Strength by the Diametral-Compression Test" Journal of Pharmaceutical Sciences, vol. 59, No. 5, May 1970, pp. 688-691.
Follonier N. et al., Drug Development and Industrial Pharmacy, 20(8), pp. 1323-1339, 1994.
Follonier, N. et al.. "Various ways of modulating the release of dltiazern hydrochloride from hot-melt extruded sustained release pellets prepared using polymeric materials" Journal of Controlled Release 36, pp. 243-250, 1995.
Freed et al., "pH Control of Nucleophilic/electrophilic oxidation", International Journal of Pharmaceutics, vol. 357, pp. 180-188 (2008).
Giles R, et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985; 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients, Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
International Search Report and Written Opinion for Application No. PCT/EP2010/004459 dated Dec. 1, 2010.
International Search Report and Written Opinion for Application No. PCT/EP2013/053894 dated Mar. 22, 2013.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Kalant H. et al., Death in Amphetamine Users: Caues and Rates, CMA Journal, vol. 112 (Feb. 8, 1975): 999-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
Knevel, Adelbert. Separation. Chapter 78. pp. 1432-1442 In Remington's Pharmaceutical Sciences, 17th Ed, 1985.
Lee, Y.-S. et al., Principles of Terahertz. Science and Technology (Lecture Notes in Physics), Springer; 1 edition 2008.(Table of Contents Only).
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharnaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2 Unersuchungen zur Optimierung der Wirkstofffreigabe" Pharmazie 45, H. 8, pp. 592-593 1990. English language translation of relevant paragraph provided.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity, J.W.—Letter of Jan. 26, 2009, pp. 1-4.
McGinty et al., Hot-Melt Extrusion as a Pharmaceutical Process, American Pharmaceutical Review, vol. 4 (2), pp. 25-36, 2001.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Miles, R.E. et al., Terahertz Frequency Detection and Identification of Materials and Objects (NATO Science for Peace and Security Series B: Physics and Biophysics), Springer; 1 edition 2007.(Table of contents).
Miller "To crush or not to crush? What to consider before giving medications to a patent with a tube or who has trouble swallowing", Nursing, pp. 50-52, Feb. 2000.
Mitchell, "Oral Dosage Forms That Should Not Be Crushed: 2000 Update" Hospital Pharmacy 35(5), 553-557, 2000.

(56) References Cited

OTHER PUBLICATIONS

Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al."Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly)ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
Pharm. Research, Official Journal of the American Association of Pharmaceutical Scientists, Oct. 1991, 8(10), 8-192.
Pharm. Research, Official Journal of the American Association of Pharmaceutical Scientists, Sep. 1989, 6(9); 6-98.
Phillips, G, Briggs. Sterilization. Chapter 79. pp. 1443-1454, In Remington's Pharmaceutical Sciences, 17th Ed, 1985.
Pillay V. et al. A novel approach for constant rate delivery of highly soluble bioactives from a simple monolithic system. Journal of Controlled Release. 2000, vol. 67, pp. 67-78.
Pinto, Joao F, et al.,"Evaluation of the Potential Use of Poly(ethylene oxide) as Tablet- and Extrudate-Forming Material," AAPS PharmSci, 2004; 6(2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington's Pharmaceutical Sciences 17th ed., Chapter 78, p. 1418 (1985).
Repka M. et al., Bioadhesive Properties of Hydroxypropylcellulose Topical Films Produced by Hot-Melt Extrusion, Journal of Controlled Release, 70 (2001), pp. 341-351.
Repka MA. Drug Dev Ind Pharm, Oct. 2007;33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Sax et al., Hawley's Condensed Chemical Dictionary, 11th ed., 1987, p. 1233, definition of "wax".
Scheirs J., et al."Characterizing of the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Plantewalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed, 1985.
Sprockel O.L et al. "Permeability of Cellulose Polymers: Water Vapour Transmission Rates"., J. Pharma. Pharmacol. 42, pp. 152-157, 190.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al"Diffusion of small molecular weight drugs in radiation—crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Tablet, www.docstoc.com (2011),
Third Party Observations filed with EPO for Patent EP65055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Turco et al. Intravenous Admixtures. Chapter 86.. pp. 1542-1552, In Reminaton's Pharmaceutica Sciences, 17th Ed, 1985.
US Pharmacopoeia, Chapter 1217, Aug. 12, 2008.

(56) References Cited

OTHER PUBLICATIONS

Varma et al, Factors Affecting Mechanism and Kinetics of Drug Release from Matrix-Based Oral Controlled Drug Delivery Systems, Am. J. Drug Deliv. 2004: 2 (1): 43-57.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Waltimo, et al, "A novel bite force recorder and maximal isometric bite force values for healthy young adults", Scandinavian Journal of Dental Research 1993; 101: 171-175.
Waltimo, et al, "Maximai bite force and its association with signs and symptoms of craniomandibular disorders in young Finnish non-patients", Acta Odontol Scand 53 (1995) : 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 1164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
Woodburn, K.R. et al., Vascular complications of injecting drug misuse, Br. J. of Surgery. vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences. vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature, 322 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zhang et al., "Properties of Sustained-Release Tablets Prepared by Hot-Melt Extrusion" Pharmaceutical Development and Technology, 1999, 4(2), 241-250.
PCT International Search Report and Written Opinion for PCT Application No. PCT/EP2013/057851 dated Jun. 12, 2013.
Application of a modeling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Evaluation of Verapamil HCl (240 mg) Extended Release Matrix Formulation Using USP Apparatus III in Biorelevant Dissolution Media, Jul. 2009.
Formulation of Polyox ER Matrices for a Highly Soluble Active, Colorcon Jul. 2009.
Metformin Hydrochloride 750 mg Extended Release Tablets, Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Physico-mechanical Characterization of Polyox for Table Manufacture, Colorcon Jul. 2009.
Tramadol Hydrochloride 100 mg Extended Release Tablets, Lubrizol Advanced Materials, Inc., Sep. 2010.
Bauer et al. Lehrbuch der Pharmazeutischen Technologie. Eight Edition 2006. Stuttgart, pp. 343-352.
Hartauer, Pharma. Dev. & Tech. 5 (3) 303-310 (2000).
Marques, Tablet breaking force. 2008.
Ritschel et al. Die Tablette. Handbuch der Entwieklung, Herstellung and Qualitatssicherung. 2nd Edition, 2002, Ch 6, pp. 69-82 and 115-136.
Ritschel et al. Die Tablette: Handbuch der Entwicklung, Herstelling und Qualitatssicherung. 2nd Edition, 2002, Table of content.
Wagner, Pharmazeutisehe Biologie—Drogen und ihre Inhaltsstoffe—Scharfstoffdrogen, 2nd., revised edition. Gustav Fischer Verlag, Stuttgart-N.Y., 1982,Table of Content.
Zeeshan, F and N. Bukhari. "Development and Evaluation of a Novel Modified-Release Pellet-Based Tablet System for the Delivery of Loratadine and Pseudophedrine Hydrochloride as Model Drugs," AAPS PharmaSciTech 11(2): 910-916 (available on-line May 22, 2010).
POLYOX water-soluble resins (DOW Mar. 2002); see http://msds-search.dow.com/PublishedLiteratureDOWCOM/dh_0031/0901b80380031a4a.pdf?filepath=/326-00001.pdf&fromPage=GetDoc).
Swarbrick, Encyclopedia of Pharmaceutical Technology, Inform Healthcare. 1988. 1st edition. vol. 1. table of contents.
Swarbrick, Encyclopedia of Pharmaceutical Technology, Informa Healthcare. 1988, 1st edition, vol. 2, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 20, table of contents.
Almeida, A. et al., Ethylene vinyl acetate as matrix for oral sustained release dosage forms produced via hot-melt extrusion, European Journal of Pharmaceutics and Biopharmaceutics 77 (2011) 297-305.

(56) References Cited

OTHER PUBLICATIONS

Almeida, A. et al., Sustained release from hot-melt extruded matrices based on ethylene vinyl acetate and polyethylene oxide, European Journal of Pharmaceutics and Biopharmaceutics 82 (2012) 526-533.

Sreenivasa, B. et al, Design and evaluation of ethylene vinyl acetate sintered matrix tablets, Indian Journal of Pharmaceutical Sciences, Sep.-Oct. 2003, 65(5): 496-502.

European Search Report and Written Opinion for EP Application No. 13169658.5, dated Aug. 6, 2013.

European Search Report and Written Opinionfor EP Application No. 13169659.3, dated Aug. 6, 2013.

PCT International Search Report and Written Opinion for PCT Application No. PCT/EP2013/059728 dated Aug. 6, 2013.

PCT International Search Report and Written Opinion for PCT Application No. PCT/EP2009/003290 dated Jul. 9, 2009.

"Polyox water soluble resins" 2003. http://www.dow.com/webapps/lit/litorder.asp?filepath=polyox/pdfs/noreg/326-00002.pdf.

Albertini, B. "New spray congealing atomizer for the microencapsulation of highly concentrated solid and liquid substances," European Journal of Pharmaceutics and Biopharmaceutics 69 (2008) 348-357.

Jannetto, P. et al, "Oxycodone: Recognition and Pharmacogenomics," Toxicology News, Mar. 2003, 1-7.

Kolter, K., "Compression Behaviour of Kollidon SR," APV/ APGI 2002, Florence, Apr. 11, 2002.

Oxycodon (Oxygesic): Missbrauch, Abhaengigkeit und toedliche Folgen durnh Injection zerstossener Retardtabletten, Deutsches Ärzteblatt, vol. 36, A2326-A2326, Sep. 5, 2003.

Oxycontin: Balancing Risks and Benefits, United States Senate, Hearing, Feb. 12, 2002.

Pontier, C. et al, "Use of cycles of compression to characterize the behavior of apatitic phosphate powders," Journal of the European Ceramic Society 22 (2002), 1205-1216.

Silver, J. "Painkiller OxyContin 'most commonly abused prescription drug on the streets of Western Pennsylvania'", Pittsburg Post-Gazette, Apr. 8, 2001.

Wikipedia—Dextromethorphan Aug. 12, 2013 (and attached related English-language entry dated Dec. 11, 2013).

Foye, W., Principles of Medicinal Chemistry; Stuctural Features and Pharmacologic Activity, pp. 63-66 at 65 (1989).

Foye, W., Principles of Medicinal Chemistry; Analgesics pp. 241-242, at 241 (1989).

Remington, The Science and Practice of Pharmacy, 19th ed., vol. II, p. 1457 (1995) (providing a table of DFA-approved commercially marketed salts).

Spassov et al., Stereochemistry of Diastereomeric 3-Dialkylaminopropanols and O-Derivatives, J.f. prakt. Chemie, 323:5, 793-800 (1981).

European Search Report and Written Opinion for EP Application No. 13176309.9-1460, dated Oct. 9, 2013.

Tranquilan-Aranilla et al., "Kappa-carrageenan-polyethylene oxide hydrogel blends prepared by gamma irradiation," Radiation Physics and Chemistry vol. 55, pp. 127-131, 1999.

Tikhonov, A. et al., Biopharmacy. The Manual for Students of Pharmaceutical Universities and Departments. 2003, pp. 40-41, Kharkov, Ukraine. (Full English translation attached.).

European Search Report and Written Opinion for EP Application No, 13197503.9-1460, dated Feb. 18, 2014.

POLYOX, Colorcon, Application Data (Apr. 2009) downloaded from http://www.colorcon.com/literature/marketing/mr/Extended%20Release/POLYOX/English/ads_PEO_Antioxidant pdf.

PCT Second Written Opinion for PCT Application No. PCT/EP2013/057851 dated Apr. 15, 2014.

Gryczke et al., "Development and evaluation of orally disintegrating tablets (ODTs) containing Ibuprofen granules prepared by hot melt extrusion", Colloids and surfaces., B; Biointerfaces, Elsevier, Amsteram, NL, vol. 86, No. 2, Apr. 5, 2011, pp. 275-284.

Li et al., "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.

European Search Report and Written Opinion for EP Application No. 13425151.1-1460, dated Mar. 11, 2014.

Dierickx et al., "Co-extrusion as manufacturing technique for fixed-dose combination mini-matrices," European Journal of Pharmaceutics and Biopharmaceutics 81 (2012), 683-689.

Eggleston, "The seat of the emetic action of various drugs," J. Pharmacol. Exp. Ther. 7, 253 (1915) 225-253 (1915).

Eudragit NE4OD web page from Evonik website; downloaded Feb. 24, 2015.

Eudragit RS PO web page from Evonik website; downloaded Feb. 24, 2015.

European Search Report and Opinion Application No. 14176277.3-1460, dated Dec. 15, 2014.

European Search Report and Written Opinion for EP Application No. 14169801.9-1455 dated Oct. 20, 2014.

Evonik Rohm GmbH product brochure: EUDRAGIT acrylic polymers for solid oral dosage forms (2009).

Glyceryl behenate monograph; European Pharmacopeia 5.0; dated Jan. 2005; downloaded Feb. 24, 2015.

Kondrat, T. , "Technology dosage forms" Moscow 1991, p. 96.

Lenindzer, A., "The molecular basis of the structure and functions of cells" Moscow 1974, p. 68.

Moorman-Li, R. et al, "A Review of Abuse-Deterrent Opioids for Chronic Nonmalignant Pain." Pharmacy and Therapeutics, vol. 37 No. 7, Jul. 2012, pp. 412-421.

Morissette et al. Advanced Drug Delivery Review 26 (2004), 275-300.

Oliveira et al., "Production and characterization of laminar coextrudates at room temperature in the absence of solvents," AAPS Annual Meeting and Exposition, Oct. 14-18, 2012, Chicago, USA.

PCT International Search Report and Written Opinion for PCT Application No. PCT/EP2014/064830 dated Aug. 6, 2014.

PCT International Search Report and Written Opinion for PCT Application No. PCT/EP2014/075618 dated Feb. 11, 2015.

Quintavalle et al., "Preparation of sustained release co-extrudates by hot-melt extrusion and mathematical modelling of in vitro/in viva drug release profiles," European Journal of Pharmaceutical Sciences 33 (2008), 282-293.

Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.

Salomies et al., "Determination of Oxycodone Hydrochloride in Oral Solutions by High-Performance Thin-Layer Chromatography/Densitometry," Journal of AOAC International, 83: 1497-1501 (2000).

Vippagunta et al. Advanced Drug Delivery Review 48 (2001), 3-26.

PCT International Search Report and Written Opinion for PCT Application No. PCT/EP2014/0777748 dated Feb. 2, 2015.

Monolithic: retrieved from internet: http:/merriam-webster.com/dictionary/monolithic. Retrieved on Sep. 2, 2015.

Extended European Search Report and Opinion for Application No. EP 15165067.8-1455, dated Nov. 2, 2015.

Extended European Search Report and Opinion for Application No. EP 15165065.2-1455, dated Nov. 2, 2015.

Extended European Search Report and Opinion for Application No. EP 15165069.4-1455, dated Nov. 2, 2015.

Extended European Search Report and Opinion for Application No. EP 15165064.5-1455, dated Oct. 16, 2015.

Extended European Search Report and Opinion for Application No. EP 15165070.2-1455, dated Nov. 2, 2015.

Extended European Search Report and Opinion for Application No. EP 15153679.4-1455, dated Jun. 30, 2015.

PCT International Search Report and Written Opinion for PCT Application No. PCT/EP2015/061343 dated Jul. 21, 2015.

PCT International Search Report and Written Opinion for PCT Application No. PCT/EP2015/060377 dated Jul. 23, 2015.

West, Anthony R., Solid state chemistry and its applications, Wiley, New York, 1988, pp. 358-365.

(56) References Cited

OTHER PUBLICATIONS

Bruce et al, Properties of hot-melt extuded tablet formulations for the colonic delivery of 5-aminosalicylic acid, European Journal of Pharmaceutics and Biopharmaceutics, 59 (2005) 85-97.
Bingwen et al, 2008, p. 367.
Bingwen et al, 2008, p. 367, (full translation attached).
Alekseeva et al, Chemical-Pharmaceutical Journal, vol. 41, No. 9, 2007, 49-52. (Full translation attached.).
Borquist et al., "Simulation of the release from a multiparticulate system validated by single pellet and dose release experiments," J. Controlled Release, 97: 453-465 (2004).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Cuesov, 1999, pp. 351-352.
Extended European Search Report and Opinion for Application No. EP 15184634.2-1455, dated Mar. 3, 2016.
Saleem et al. "Formulation and Evaluation of Tramadol hydrochloride Rectal Suppositories," Indian J. Pharm Sci. Sep.-Oct. 2008; 70(5), 640-644.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Verhoeven et al., "Influence of polyethylene glycol/polyethylene oxide on the release characteristics of sustained-release ethylcellulose mini-matrices produced by hot-melt xtrusion: in vitro and in vivo evaluations," European Journal of Pharmaceutics and Biopharmaceutics 72 (2009) 463-470.
Verhoeven, et al. "Xanthan gum to tailor drug release of sustained-release thylcellulose mini-matrices prepared via hotmelt extrusion: in vitro and in vivo evaluation," European Journal of Pharmaceutics and Biopharmaceutics, 63 (2006) 320-330.
Vynckier et al.,"Hot-melt co-extrusion for the production of fixed-dose combination products with a controlled release ethylcellulose matrix core," International Journal of Pharmaceutics 464 (2014), 65-74.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Extended European Search Report for Application No. EP 16183922.0-1460, dated Oct. 31, 2016.
Cuesov, Drug Production Technology, Khar'kov, 1999, pp. 351-352.
Efentakis et al, Effects of Excipients on Swellin and Drug Release from Compressed Matrices, in Drug Development and Industrial Pharmacy 23(1)107-112, Jan. 1997, Abstract.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Fathima, N. et al. "Drug-excipient interaction and its importance in dosage form evelopment," Journal of Applied Pharmaceutical Science 01 (06); 2011, pp. 66-71.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Remington, Chapter 45, pp. 996-1035.
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.

U.S. Court of Appeals, Federal Circuit, *Purdue Pharma L.P.* v. *Epic Pharma, LLC*, 117 USPQ2d 1733 (Fed. Cir. 2016).
Decision of the United States District Court for the Southern District of New York, in *In re Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in *In re Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, Tastes in and Tastes of Paprika, in Taste: Proceedings of the Oxford Symposium on Food and Cookery 28 (Tom Jaine Ed. 1988).
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18: 154-156 (May/Jun. 2001).
Choi, S. et al, "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Choi, S.U., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley M. et al. Pharmaceutical Applications of Hot-Melt Extrusion: Part I. Drug Dev. & Indus. Pharmacy (2007) 33:909-926.
Crowley M., "Physicochemical and Mechanical Characterization of Hot-Melt Extruded Dosage Forms." Dissertation presented to the Faculty of the Graduate School of the University of Texas at Austin. (May 2003).
Crowley, M. et al., "Properties of Hot-Melt Extruded CPM Tablets Using Hydrophilic Polymers," poster presentation, (2000).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001-CROWLEY0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.

(56) References Cited

OTHER PUBLICATIONS

Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/211211bl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int'l J Pharmaceutics (1997) 147:199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and isintegration of paracetamol and oxytetracylcine tablets," J Pharm Pharmac., 9:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.
Rauwendaal, Chris, Phd, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci., 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Extended European Search Report for Application No. EP 16182124.4-1455, dated Jan. 17, 2017.
USP Expert Council, US Pharmacopoeia, Chapter 1092, 2007, 1-15.
Dabbagh, et al. "Release of Propranolol Hydrochloride from Matrix Tablets Containing Sodium Carboxymethylcellulose and Hydroxypropylniethylcellulose"; 1999; Pharmaceutical Development and Technology, 4(3), 313-324.
Remington, Chapter 45, pp. 996-1035. (2000) (Full Translation Attached).

(56) References Cited

OTHER PUBLICATIONS

M. Xu et al., "Evaluation of the coat quality of sustained release pellets by individual pellet dissolution methodology," Int. J. Pharm. 478 (2015) 318-327.
Bannwarth, Bernard, "Will Abuse-Deterrent Formulations of Opioid Analgesics be Successful in Achieving Their Purpose?", Drugs, 2012, vol. 72, pp. 1713-1723.
Pharma Tips ([online] retrieved on Mar. 22, 2018 from http://ww.pharmatips.in/Articles/Pharmaceutics/Tablet/Co-Processed-Directly-Compresses-Adjutants.aspx May 2011: 10 pages).
POLYOX Water-Soluble Resins in Pharmaceutical Application. Dow Chemicals. Published 2004.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
European Search Report and Written Opinion for EP Application No. 13197503.9-1460, dated Feb. 18, 2014.
Investigation of a Directly Compressible Metformin HCl 500mg Extended Release Formulation Based on Hypromellose, Colorcon Jul. 2009.
Koziolek, M. et al., "Development of a bio-relevant dissolution test device simulating mechanical aspects present in the fed stomach," European Journal of Pharmaceutical Sciences 57 (2014) 250-256.
Nickerson, B., Sample Preparation of Pharmaceutical Dosage Forms, Springer, New York (2011); Chapter 1, pp. 3-48.
PCT International Search Report and Written Opinion for PCT Application No. PCT/EP2016/052046 dated Apr. 12, 2016.
Furu et al. "use of ADHD drugs in the Nordic countries: a population-based pomparison study," Acta Psychiatrica Scandinavia, May 2010.
COMPAP 90 technical data sheet Mar. 2014; 1 page.
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd, "Certificate of Analysis," Product: Polyethylene Oxide; Grade: PEO-20NF; Feb. 3, 2016.
Sumitomo Seika Chemicals, Co., Ltd, "Certificate of Analysis," Product: Polyethylene Oxide; Grade: PEO-20NF; May 15, 2013.
Sumitomo Seika Chemicals, Co., Ltd, "Certificate of Analysis," Product: Polyethylene Oxide; Grade: PEO-20NF; Jan. 23, 2012.
De Brabander, C. et al., "Development and evaluation of sustained release mini-matrices prepared via hot melt extrusion," Journal of Controlled Release 89 (2003), 235-247.
PCT International Search Report and Written Opinion for PCT Application No. PCT/EP2017/070396 dated Sep. 8, 2017.
U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.
European Pharmacopoeia 3.0, 2.9.8 "Resistance to Cruching of Tablets", 1997, p. 135.
Goodman and Gilman, 1985, 7th edition, chapter 29, 674-715.
King, Remington's Pharmaceutical Sciences 17th ed., Chapter 78, p. 1418-1419 (1985).
Quadros, E. et al., "Evaluation of a novel colonic delivery device in vivo," STP Pharma Sci. 5, 77-82 (1995).
Theeuwes, Felix et al., Osmotic Systems for Colon-Targeted Drug Delivery in Colonic Drug Absorption and Metabolism (Peter R. Bieck ed., 1993).
Wooten, Marvin R. et al., Intracerebral Hemorrhage and Vasculitis Related to Ephedrine Abuset 13 Annals of Neurology 337 (1983).

\* cited by examiner

THERMOFORMED, TAMPER-RESISTANT PHARMACEUTICAL DOSAGE FORM CONTAINING ZINC

This application claims priority of U.S. Provisional Patent Application No. 61/645,659, filed on May 11, 2012, and European Patent Application No. 12 003 743.7, filed on May 11, 2012, the entire contents of which patent applications are incorporated herein by reference.

The invention relates to a thermoformed, tamper-resistant pharmaceutical dosage form comprising a pharmacologically active ingredient; a polyalkylene oxide having a weight average molecular weight of more than 200,000 g/mol; and a zinc component, wherein the content of said zinc component is at least 1 ppm, relative to the total weight of the pharmaceutical dosage form.

Many pharmacologically active ingredients have a potential of being abused and thus, are advantageously provided in form of tamper resistant pharmaceutical dosage forms. Prominent examples of such pharmacologically active ingredients are opioids.

It is known that abusers crush conventional tablets, which contain opioids, to defeat the time-release "micro-encapsulation" and then ingest the resulting powder orally, intranasally, rectally, or by injection.

Various concepts for the avoidance of pharmacologically active ingredient abuse have been developed. One concept relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded.

Such pharmaceutical dosage forms are useful for avoiding pharmacologically active ingredient abuse of the pharmacologically active ingredient contained therein, as they may not be powdered by conventional means and thus, cannot be administered in powdered form, e.g. nasally. The mechanical properties, particularly the high breaking strength of these pharmaceutical dosage forms renders them tamper resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884 (corresponding to US 2006/0002860), WO 2006/002886, WO 2006/082097, WO 2006/082099, WO 2008/107149, WO 2009/092601, and WO 2011/009 603.

Methods and compositions for deterring abuse of orally administered pharmaceutical products are disclosed in WO 2006/058 249 and EP 2 402 004.

The release kinetics of the pharmacologically active ingredients from such tamper-resistant dosage forms is an important factor. It is well known that depending on how a pharmaceutically pharmacologically active ingredient is formulated into a tablet its release pattern can be modified.

On the one hand, formulations providing immediate release upon oral administration have the advantage that they lead to a fast release of the pharmacologically active ingredient in the gastrointestinal tract. As a result, a comparatively high dose of the pharmacologically active ingredient is quickly absorbed leading to high plasma levels within a short period of time and resulting in a rapid onset of medicinal action, i.e. medicinal action begins shortly after administration. At the same time, however, a rapid reduction in the medicinal action is observed, because metabolization and/or excretion of the pharmacologically active ingredient cause a decrease of plasma levels. For that reason, formulations providing immediate release of pharmacologically active ingredients typically need to be administered frequently, e.g. six times per day. This may cause comparatively high peak plasma pharmacologically active ingredient concentrations and high fluctuations between peak and trough plasma pharmacologically active ingredient concentrations which in turn may deteriorate tolerability.

Controlled release (e.g. delayed release, prolonged release, sustained release, and the like) may be based upon various concepts such as coating the pharmaceutical dosage form with a controlled release membrane, embedding the pharmacologically active ingredient in a matrix, binding the pharmacologically active ingredient to an ion-exchange resin, forming a complex of the pharmacologically active ingredient, and the like. In this context it can be referred to, e.g., W. A. Ritschel, Die Tablette, 2. Auflage, Editio Cantor Verlag Aulendorf, 2002.

In comparison to formulations providing immediate release, formulations providing prolonged release upon oral administration have the advantage that they need to be administered less frequently, typically once daily or twice daily. This can reduce peak plasma pharmacologically active ingredient concentrations and fluctuations between peak and trough plasma pharmacologically active ingredient concentrations which in turn may improve tolerability.

The ideal goal in designing a prolonged-release system is to deliver the pharmacologically active ingredient to the desired site at a rate according to the needs of the body. In the absence of feed-back control, one is left with a simple prolonging effect, where the pivotal question is at what rate a pharmacologically active ingredient should be delivered to maintain a constant blood pharmacologically active ingredient level. This constant rate should be the same as that achieved by continuous intravenous infusion where a pharmacologically active ingredient is provided to the patient at a constant rate just equal to its rate of elimination. This implies that the rate of delivery must be independent from the amount of pharmacologically active ingredient remaining in the pharmaceutical dosage form and constant over time.

A perfectly invariant pharmacologically active ingredient blood or tissue level versus time profile is the ideal starting goal of a prolonged-release system. The way to achieve this, in the simplest case, is use of a maintenance dose that releases its pharmacologically active ingredient by zero-order kinetics.

U.S. Pat. No. 5,082,668 discloses an osmotically driven dosage form, namely a device comprising a wall that surrounds a compartment. The compartment comprises a beneficial agent composition and a push composition. A passageway in the wall connects the compartment with the exterior of the device for delivering the beneficial agent at a rate governed, in combination, by the wall, the beneficial agent composition and the push composition through the passageway of the device over time.

U.S. Pat. No. 7,300,668 relates to a dosage form comprising: a three-dimensionally printed innermost region comprising a first regional concentration of at least one active pharmaceutical ingredient; and plural three-dimensionally printed non-innermost regions in nested arrangement and comprising: a) one or more nested internal regions, wherein an internal region completely surrounds and is in contact with the innermost regions, and any other internal region present completely surrounds another internal region located to the interior thereof; and b) an outermost region completely surrounding an internal region, wherein the internal and outermost regions are in nested arrangement, wherein the at least one active pharmaceutical ingredient is released in approximately a zero-order release.

WO 2008/086804 discloses abuse resistant polyglycol-based pharmaceutical compositions. The composition contains one or more polyglycols and one or more active substances and it is resistant to crushing, melting and/or extraction. Moreover, such compositions have the same or lower solubility in ethanolic-aqueous medium, i.e. they are not subject to ethanol-induced dose dumping effect.

WO 2008/148798 discloses a layered pharmaceutical composition suitable for oral use in the treatment of diseases where absorption takes place over a large part of the gastrointestinal tract.

WO 03/024426 discloses a controlled release pharmaceutical composition for oral use comprising a solid dispersion of: i) at least one therapeutically, prophylactically and/or diagnostically active substance, which at least partially is in an amorphous form, ii) a pharmaceutically acceptable polymer that has plasticizing properties, and iii) optionally, a stabilizing agent, the at least one active substance having a limited water solubility, and the composition being designed to release the active substance with a substantially zero order release. Zero order release is provided by a coating that remains intact during the release phase and covers the matrix composition in such a manner that only a specific surface area is subject to erosion. Thereby the surface area from which the active substance is released is kept substantially constant during the time period.

WO 2010/057036 discloses a solid composition and methods for making and using the solid composition are provided. The solid composition comprises: (a) at least one active agent with a solubility of less than about 0.3 mg/ml in an aqueous solution with a pH of at most about 6.8 at a temperature of about 37° C.; and (b) a hydrophilic polymer matrix composition comprising: i) a hydrophilic polymer selected from the group consisting of METHOCEL®, POLYOX® WSR 1105 and combinations thereof; and optionally ii) a hydrophobic polymer selected from the group consisting of Ethocel 20 premium; and (c) an alkalizer selected from the group consisting of calcium carbonate, magnesium oxide heavy and sodium bicarbonate; wherein the composition provides at least about 70% release of the active between about 7 to about 12 hours following oral administration.

WO 2005/105036 discloses controlled release oral pharmaceutical mucoadhesive matrix formulation containing a therapeutically effective amount of tolterodine or its pharmaceutically acceptable salts, prodrugs and metabolites thereof dispersed in a rate controlling polymeric matrix comprising (1) a pH independent gelling polymer, such as polyethylene oxide, (2) a pH dependent gelling polymer, such as sodium of carboxymethylcellulose, (3) a film coating polymer component, such as Eudragit RS100 and other conventional tablet functional excipients.

V. Pillay et al., Journal of Controlled Release, 67 (2000) 67-78 disclose an approach for constant rate delivery of highly soluble bioactives from a simple monolithic system prepared by direct compression at ambient conditions.

M. E. McNeill et al., J Biomater Sci Polym 1996, 7(11), 953-63 relate to properties controlling the diffusion and release of water-soluble solutes from poly(ethylene oxide) hydrogels. Part 4 deals with extended constant rate release from partly-coated spheres.

D. Henrist et al. relate to in vitro and in vivo evaluation of starch-based hot stage extruded double matrix systems. The objective of developing a double matrix system consisting of a hot stage extruded starch pipe surrounding a hot stage extruded and drug-containing starch core, was to obtain a monolithic matrix system applicable in the domain of sustained drug release. The behaviour of the systems was evaluated through dissolution testing and through a randomised crossover bioavailability study on nine male volunteers. All double matrix systems showed in vitro a nearly constant drug release profile after an initial slower release phase of 4 h. This initial slower release phase was avoided by loading the starch pipe with a small amount of drug.

L. Yang et al., J. Pharm. Sciences, 85(2), 1996, 170-173 relate to zero-order release kinetics from a self-correcting floatable asymmetric configuration drug delivery system.

It is an object of the invention to provide pharmaceutical dosage forms having advantages compared to pharmaceutical dosage forms of the prior art.

This object has been achieved by the subject-matter described hereinbelow.

It has been surprisingly found that polyalkylene oxide compositions which are composed of a polyalkylene oxide having a weight average molecular weight of more than 200,000 g/mol and a zinc component are useful in the manufacture of pharmaceutical dosage forms and have advantages compared to the polyalkylene oxide compositions of the prior art. In particular, it has been surprisingly found that aqueous dispersions of polyalkylene oxide compositions which are composed of a polyalkylene oxide having a weight average molecular weight of more than 200,000 g/mol and a zinc component have lower pH values than aqueous dispersions of polyakylene oxide compositions containing substantially no zinc component. It appears that the lower pH value can enhance the stability of the pharmacologically active ingredients and the polyalkylene oxide polymers that are contained in the pharmaceutical dosage forms. Thus, there is evidence that polyalkylene oxide compositions which are composed of a polyalkylene oxide having a weight average molecular weight of more than 200,000 g/mol and a zinc component have positive effects on the shelf life of the pharmaceutical dosage forms.

A first aspect of the invention relates to a thermoformed, tamper-resistant pharmaceutical dosage form comprising a) a pharmacologically active ingredient;
b) a polyalkylene oxide having a weight average molecular weight of more than 200,000 g/mol; and
c) a zinc component, wherein the content of said zinc component is at least 1 ppm, relative to the total weight of the pharmaceutical dosage form.

The pharmaceutical dosage form according to the invention contains a pharmacologically active ingredient.

For the purpose of specification, the term "pharmacologically active ingredient" may refer to either one or more pharmacologically active ingredients. There are generally no limitations as to the pharmacologically active ingredient (pharmacologically active compound) which can be incorporated into the pharmaceutical dosage form according to the invention.

In a preferred embodiment, the pharmaceutical dosage form contains only a single pharmacologically active ingredient. In another preferred embodiment, the pharmaceutical dosage form contains a combination of two or more pharmacologically active ingredients.

Preferably, the pharmacologically active ingredient has potential for being abused. Pharmacologically active ingredients with potential for being abused are known to the person skilled in the art and comprise e.g. tranquillizers, stimulants, barbiturates, narcotics, opioids or opioid derivatives.

Preferably, the pharmacologically active ingredient exhibits psychotropic action.

Preferably, the pharmacologically active ingredient is selected from the group consisting of opioids, stimulants, tranquilizers, and other narcotics.

Particularly preferably, the pharmacologically active ingredient is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

The following opioids, tranquillizers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papavereturn, pernoline, pentazocine, pentobarbital, pethidine, phenadoxone, phenomorphane, phenazocine, phenoperidine, piminodine, pholcodine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)-methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl) propionate, (RR—SS)-2-acetoxy-4-trifluoromethyl-benzoic acid 3-(2-dimethylaminomethyl-1-hydroxycyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxybenzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxycyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the pharmaceutical dosage form according to the invention contains an opioid selected from the group consisting of DPI-125, M6G (CE-04-410), ADL-5859, CR-665, NRP290 and sebacoyl dinalbuphine ester.

In a preferred embodiment, the pharmaceutical dosage form according to the invention contains one pharmacologically active ingredient or more pharmacologically active ingredients selected from the group consisting of oxymorphone, hydromorphone, morphine and the physiologically acceptable salts thereof.

In another preferred embodiment, the pharmacologically active ingredient is selected from the group consisting of tapentadol, faxeladol, axomadol and the physiologically acceptable salts thereof.

In still another preferred embodiment, the pharmacologically active ingredient is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)-pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active ingredient may be present in form of a physiologically acceptable salt, e.g. physiologically acceptable acid addition salt.

Physiologically acceptable acid addition salts comprise any acid addition salts which can conveniently be obtained by treating the base form of the pharmacologically active ingredient with appropriate organic and inorganic acids. Pharmacologically active ingredients containing an acidic proton may be converted into their non-toxic metal or amine addition salt forms by treatment with appropriate organic and inorganic bases. The term addition salt also comprises the hydrates and solvent addition forms which the pharmacologically active ingredients are able to form. Examples of such forms are e.g. hydrates, alcoholates and the like.

Unless explicitly stated otherwise, all amounts of the pharmacologically active ingredient specified in the following are given according to the corresponding amount of the free compound.

The pharmacologically active ingredient is present in the pharmaceutical dosage form in a therapeutically effective amount. The amount that constitutes a therapeutically effective amount varies according to the pharmacologically active ingredients being used, the condition being treated, the severity of said condition, the patient being treated, and whether the pharmaceutical dosage form is designed for an immediate or retarded release. The amount of pharmacologically active ingredient(s) used in the present invention preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the pharmaceutical dosage form.

The content of the pharmacologically active ingredient in the pharmaceutical dosage form is not limited. The dose of the pharmacologically active ingredient which is adapted for administration preferably is in the range of 0.1 mg to 2,000 mg or 0.1 mg to 1,000 mg or 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient which is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg. In another preferred embodiment, the total amount of the pharmacologically active ingredient that is contained in the pharmaceutical dosage form is within the range of from 10 to 500 mg, more preferably 12 to 450 mg, still more preferably 14 to 400 mg, yet more preferably 16 to 350 mg, most preferably 18 to 325 mg and in particular 20 to 300 mg.

Preferably, the content of the pharmacologically active ingredient is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of pharmacologically active ingredient is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of pharmacologically active ingredient is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of pharmacologically active ingredient is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

In a preferred embodiment, the pharmacologically active ingredient is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the pharmacologically active ingredient is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg. In still another preferred embodiment, the pharmacologically active ingredient is contained in the pharmaceutical dosage form in an amount of 250±10 mg, 275±10 mg, 300±10 mg, 325±10 mg, 350±10 mg, 375±10 mg, 400±10 mg, 425±10 mg, 450±10 mg, 475±10 mg, 500±10 mg, 525±10 mg, 550±10 mg, 575±10 mg or 600±10 mg.

Preferably, the pharmaceutically dosage form provides a release of the pharmacologically active ingredient after 1 hour of preferably at most 60%, more preferably at most 40%, yet more preferably at most 30%, still more preferably at most 20% and most preferably at most 17%; after 2 hours preferably at most 80%, more preferably at most 60%, yet more preferably at most 50%, still more preferably at most 40% and most preferably at most 32%; after 3 hours preferably at most 85%, more preferably at most 65%, yet more preferably at most 55%, still more preferably at most 48% and most preferably at most 42%; after 4 hours preferably at most 90%, more preferably at most 75%, yet more preferably at most 65%, still more preferably at most 55% and most preferably at most 49%; after 7 hours preferably at most 95%, more preferably at most 85%, yet more preferably at most 80%, still more preferably at most 70% and most preferably at most 68%; after 10 hours preferably at most 99%, more preferably at most 90%, yet more preferably at most 88%, still more preferably at most 83% and most preferably at most 80%; and after 13 hours preferably at most 99%, more preferably at most 95%, yet more preferably at most 93%, still more preferably at most 91% and most preferably at most 89%.

In a particularly preferred embodiment, the pharmacologically active ingredient is tapentadol, preferably its HCl salt, and the pharmaceutical dosage form is adapted for administration once daily or twice daily. In this embodiment, the pharmacologically active ingredient is preferably contained in the pharmaceutical dosage form in an amount of from 25 to 250 mg.

In another particularly preferred embodiment, the pharmacologically active ingredient is oxymorphone, preferably its HCl salt, and the pharmaceutical dosage form is adapted for administration twice daily. In this embodiment, the pharmacologically active ingredient is preferably contained in the pharmaceutical dosage form in an amount of from 5 to 40 mg. In another particularly preferred embodiment, the pharmacologically active ingredient is oxymorphone, preferably its HCl salt, and the pharmaceutical dosage form is adapted for administration once daily. In this embodiment, the pharmacologically active ingredient is preferably contained in the pharmaceutical dosage form in an amount of from 10 to 80 mg.

In another particularly preferred embodiment, the pharmacologically active ingredient is oxycodone, preferably its HCl salt, and the pharmaceutical dosage form is adapted for administration twice daily. In this embodiment, the pharmacologically active ingredient is preferably contained in the pharmaceutical dosage form in an amount of from 5 to 80 mg. In another particularly preferred embodiment, the pharmacologically active ingredient is oxycodone, preferably its HCl salt, and the pharmaceutical dosage form is adapted for administration once daily. In this embodiment, the pharmacologically active ingredient is preferably contained in the pharmaceutical dosage form in an amount of from 10 to 320 mg.

In still another particularly preferred embodiment, the pharmacologically active ingredient is hydromorphone, preferably its HCl salt, and the pharmaceutical dosage form is adapted for administration twice daily. In this embodiment, the pharmacologically active ingredient is preferably contained in the pharmaceutical dosage form in an amount of from 2 to 52 mg. In another particularly preferred embodiment, the pharmacologically active ingredient is hydromorphone, preferably its HCl salt, and the pharmaceutical dosage form is adapted for administration once daily. In this embodiment, the pharmacologically active ingredient is preferably contained in the pharmaceutical dosage form in an amount of from 4 to 104 mg.

In yet another particularly preferred embodiment, the pharmacologically active ingredient is tramadol, preferably its HCl salt, and the pharmaceutical dosage form is adapted for administration twice daily. In this embodiment, the pharmacologically active ingredient is preferably contained in the pharmaceutical dosage form in an amount of from 5 to 300 mg. In another particularly preferred embodiment, the pharmacologically active ingredient is tramadol, preferably its HCl salt, and the pharmaceutical dosage form is adapted for administration once daily. In this embodiment, the pharmacologically active ingredient is preferably contained in the pharmaceutical dosage form in an amount of from 10 to 500 mg.

The pharmaceutical dosage form according to the invention is characterized by excellent durability of the pharmacologically active ingredient. Preferably, after storage for 4 weeks, more preferably 6 months, at 40° C. and 75% rel. humidity, the content of pharmaceutical active ingredient amounts to at least 98.0%, more preferably at least 98.5%, still more preferably at least 99.0%, yet more preferably at least 99.2%, most preferably at least 99.4% and in particular at least 99.6%, of its original content before storage.

Furthermore, the pharmaceutical dosage form according to the invention is characterized by excellent durability of the polyalkylene oxide. Preferably, after storage for 6 months at 40° C. and 75% rel. humidity, the content of polyalkylene oxide amounts to at least 98.0%, more preferably at least 98.5%, still more preferably at least 99.0%, yet more preferably at least 99.2%, most preferably at least 99.4% and in particular at least 99.6%, of its original content before storage.

Suitable parameters for observing the degradation of polyalkylene oxide upon storage include the viscosity of an aqueous gel of the pharmaceutical dosage form or the content of antioxidant in the pharmaceutical dosage form, if applicable. When the polymer chains of the polyalkylene oxide deteriorate, the viscosity of an aqueous gel of the pharmaceutical dosage form decreases. The aqueous gel of the pharmaceutical dosage form is preferably prepared as described in the experimental section. Since the degradation of polyalkylene oxide is an oxidative process, it may also be followed by a decrease of the content of antioxidant, if applicable.

In a preferred embodiment, after storage for 6 months at 40° C. and 75% rel. humidity, the viscosity of the aqueous gel of the pharmaceutical dosage form according to the invention decreases by at most 15%, more preferably at most 12%, still more preferably at most 10%, even more preferably at most 8%, yet more preferably at most 7 or 6%, most preferably at most 4% and in particular at most 2 or 1% with respect to the viscosity of the aqueous gel of the pharmaceutical dosage form before storage.

In a preferred embodiment, when the pharmaceutical dosage form according to the invention contains an antioxidant, preferably α-tocopherol, the relative weight content of antioxidant in the pharmaceutical dosage form after storage for 6 months at 40° C. and 75% rel. humidity, decreases by at most 19 wt.-%, more preferably at most 18 wt.-%, still more preferably at most 17 wt.-%, even more preferably at most 16 wt.-%, yet more preferably at most 15 wt.-%, most preferably at most 10 wt.-% and in particular at most 5 wt.-% with respect to the relative weight content of antioxidant in the pharmaceutical dosage form before storage.

Suitable methods for measuring the content of the pharmacologically active ingredient, the polyalkylene oxide and antioxidant in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers, preferably as described in the experimental section, most preferably being equipped with an oxygen scavenger, in particular with an oxygen scavenger that is effective even at low relative humidity.

In a preferred embodiment, the pharmaceutical dosage form according to the invention displays improved durability of the pharmacologically active ingredient and/or the polyalkylene oxide in particular at accelerated storage conditions at 40° C. and 75% r.h., while the improved durability of the pharmacologically active ingredient and/or the polyalkylene oxide is preferably less pronounced at milder storage conditions, such as at 25° C./60% r.h. or at 30° C./65% r.h.

The pharmaceutical dosage form according to the invention contains a polyalkylene oxide and a zinc component.

Preferably, the polyalkylene oxide is selected from polymethylene oxide, polyethylene oxide and polypropylene oxide, or copolymers or mixtures thereof.

The polyalkylene oxide has a weight average molecular weight ($M_W$), preferably also a viscosity average molecular weight ($M_\eta$) of more than 200,000 g/mol or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Preferably, the molecular weight dispersity $M_W/M_\eta$ of the polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 mPa·s, more preferably 55 to 17,600 mPa·s, still more preferably 600 to 17,600 mPa·s, yet more preferably 4,500 to 17,600 mPa·s, even more preferably 4,500 to 12,000 mPa·s, most preferably 5,000 to 10,500 mPa·s and in particular 5,500 to 7,500 mPa·s or 7,500 to 10,000 mPa·s, measured in a 1 wt.-% aqueous solution.

The polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of specification, a polyalkylene glycol has a molecular weight of up to 20,000 g/mol whereas a polyalkylene oxide has a molecular weight of more than 20,000 g/mol. The weight average over all molecular weights of all polyalkylene oxides that are contained in the pharmaceutical dosage form is more than 200,000 g/mol. Thus, polyalkylene glycols, if any, are preferably not taken into consideration when determining the weight average molecular weight of polyalkylene oxide.

For the purpose of specification, the term "zinc component" is meant to include elemental zinc as well as any kind of zinc containing component, e.g. inorganic or organic salts, complexes, alloys, oxides, chelates and organozinc compounds. Furthermore, the term "zinc component" comprises polymers which contain zinc, i.e. covalently bound, in ionic form or intercalated in form of a further zinc containing component.

In a preferred embodiment, the zinc component is or comprises an organo-zinc compound of the general formula $R_2Zn$ in which preferably R respectively independently stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl; wherein "aliphatic" respectively is a branched or unbranched, saturated or a mono- or polyunsaturated, unsubstituted or mono- or polysubstituted, aliphatic hydrocarbon residue; "cycloaliphatic" respectively is a saturated or a mono- or polyunsaturated, unsubstituted or mono- or polysubstituted, alicyclic, mono- or multicyclic hydrocarbon residue; wherein with respect to "aliphatic" and "cycloaliphatic", "mono- or polysubstituted" means the mono- or polysubstitution of one or more hydrogen atoms by substituents selected independently of one another from the group consisting of —F, —Cl, —Br, —I, —CN, —$NO_2$, —CHO, —O, —R, —C(=O)R, —C(=O)H, —C(=O)OH, —C(=O)OR, —C(=O)$NH_2$, —C(=O)NHR, —C(=O)N(R)$_2$, —OH, —OR, —OC(=O)H, —OC(=O)R, —OC(=O)OR, —OC(=O)NHR, —OC(=O)$NR_2$, —SH, —SR, —$SO_3H$, —S(=O)$_{1-2}$—R, —S(=O)$_{1-2}NH_2$, —$NH_2$, —NHR, —$NR_2$, —$N^+R_3$, —$N^+(R)_2O^-$, —NHC(=O)R, —NHC(=O)OR, —NHC(=O)$NH_2$, —NHC(=O)NHR, —NH—C(=O)$NR_2$, —$SiR_3$ and —PO(OR)$_2$ with each "R" as defined above; "aryl", respectively independently, stands for a carbocyclic ring system with at least one aromatic ring, but without heteroatoms in this ring, wherein, optionally, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl; "heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system; wherein with respect to "aryl" and "heteroaryl", "mono- or polysubstituted" means the mono- or polysubstitution of one or more hydrogen atoms of the ring system by substituents selected from the group consisting of —F, —Cl, —Br, —I, —CN, —$NO_2$, —CHO, —O, —R, —C(=O)R, —C(=O)H, —C(=O)OH, —C(=O)OR, —C(=O)$NH_2$, —C(=O)NHR, —C(=O)—$NR_2$, —OH, —O($CH_2$)$_{1-2}$O—, —OR, —OC(=O)H, —OC(=O)R, —OC(=O)OR, —OC(=O)NHR, —OC(=O)$NR_2$, —SH, —SR, —$SO_3H$, —S(=O)$_{1-2}$—R, —S(=O)$_{1-2}NH_2$, —$NH_2$, —NHR, —$NR_2$, —$N^+R_3$, —$N^+R_2O^-$, —NHC(=O)R, —NHC(=O)OR, —NH—C(=O)$NH_2$, —NHC(=O)NHR, —NHC(=O)$NR_2$, —$SiR_3$ or —PO(OR)$_2$ with each "R" as defined above; wherein any N-ring atoms present can be respectively oxidized.

More preferably, R respectively independently stands for (i) an alkyl group containing from 1 to about 8 carbon atoms, preferably 1 to 6 carbon atoms, and most preferably 2 or 3 carbon atoms, or (ii) phenyl or naphthyl, or alkyl-substituted phenyl or naphthyl groups in which the alkyl groups contain from 1 to about 3 carbon atoms, or (iii) cycloalkyl groups containing from 4 to 6 ring carbon atoms; or (iv) the dicyclopentadienyl group; or (v) an alkoxide group containing from 1 to about 8 carbon atoms. Examples include, but are not limited to zinc carboxylates (e.g. zinc glutarate, zinc adipate, zinc isophthalate, zinc propionate), zinc alkyl, zinc alkoxide of monohydric and/or polyhydric alcohols, zinc cycloalkyl, zinc aryl or dicyclopentadienyl compounds (e.g. dimethylzinc, diethylzinc, dipropylzinc, di-isopropylzinc, dibutylzinc, di-isobutylzinc, di-t-butylzinc, dipentylzinc salts, dihexyl- and diheptyl- and dioctylzinc salts, di-2-ethylhexylzinc, diphenylzinc, ditolylzinc, dicyclobutylzinc, dicyclopentylzinc, di-methylcyclopentylzinc, dicyclohexylzinc, methyl phenylzinc, methyl tolylzinc, methyl naphthylzinc, ethyl phenylzinc), zinc salts of a strong acid (e.g. zinc nitrate) or an organic acid (e.g. zinc acetylacetonate, zinc acetate, zinc salts of fatty acids), zinc phthalocyanines, zinc halides, organic zinc halides (e.g. alkyl or aryl zinc halides), zinc naphthalocyanines, zinc porphyrins, zinc (meth)acrylates (e.g. zinc acrylate, zinc diacrylate, zinc methacrylate, zinc dimethacrylate), halogenated thiophenol zinc salts (e.g. zinc salt of pentachlorothiophenol), and mixtures thereof.

In a preferred embodiment, the polyalkylene oxide is obtainable by polymerizing alkylene oxide in the presence of the zinc component of the general formula $R_2Zn$. Particularly preferably, the polyalkylene oxide is obtainable by polymerizing alkylene oxide in the presence of the zinc component, wherein the zinc component is a zinc alkoxide of monohydric and/or polyhydric alcohols.

In another preferred embodiment, the polyalkylene oxide is obtainable by polymerizing alkylene oxide in the presence of the zinc component, wherein the amount of the zinc component is in the range of from 0.01 to 1 mol-% based on the zinc atom content per mol of the alkylene oxide monomers.

If the polyalkylene oxide is obtained by polymerizing alkylene oxide in the presence of the zinc component, the zinc component is preferably present in a deactivated form after the polymerization reaction, most preferably in a hydrolyzed form and even more preferably as $Zn(OH)_2$, $Zn(OH)_4^{2-}$, ZnO or mixtures thereof.

In a preferred embodiment, the zinc component comprises substantially no zinc stearate and/or zinc sulfate. In a particularly preferred embodiment, the pharmaceutical dosage form according to the invention comprises substantially no zinc stearate and/or zinc sulfate.

For the purpose of specification, unless expressly stated otherwise, "substantially no" is preferably to be regarded as below 1 ppm relative to the total weight of the dosage form, more preferably below 0.1 ppm relative to the total weight of the dosage form, still more preferably "not detectable", i.e. below the detection limit.

In a preferred embodiment, the zinc component is or comprises the reaction product of a dihydrocarbyl zinc compound and a linear alkanediol such as 1,4-butanediol. Such reaction products are useful as catalysts in the polymerization of cyclic oxides such as ethylene oxide and are known for example from U.S. Pat. No. 4,667,013, which is hereby incorporated as reference.

In another preferred embodiment the zinc component is or comprises the reaction product of a dihydrocarbyl zinc compound and an emulsion of a polyol-surfactant-dispersion aid. Such reaction products are useful as catalysts in the polymerization of alkylene oxides and are known for example from EP 0 239 973, which is hereby incorporated as reference.

In still another preferred embodiment, the zinc component is obtainable by reacting
 a dialkyl zinc (e.g. dimethyl zinc, diethyl zinc, dipropyl zinc or dibutyl zinc), diphenyl zinc or dicyclobutyl zinc
with
 an aliphatic polyhydric alcohol (e.g. ethylene glycol, propylene glycol, 1,2-butanediol, 1,3-butanediol, 1,4-butanediol, 2,3-butanediol, 1,5-pentanediol, 2,3,4-pentanetriol, glycerol or pentaerythritol), and
 a monohydric alcohol (e.g. methanol, ethanol, propanol, butanol or pentanol).

According to this embodiment, the zinc component is preferably obtainable as is described in U.S. Pat. No. 5,326,852 and U.S. Pat. No. 6,979,722, both which are hereby incorporated by reference.

In a further preferred embodiment, the zinc component is the remainder of the polymerization catalyst that was used in the course of the polymerization of the polyalkylene oxide when the polyalkylene oxide was manufactured, wherein preferably the amount of the zinc component is in the range of from 0.01 to 1 mol-% based on the zinc atom content per mol of the alkylene oxide units contained in the polyalkylene oxide. According to this embodiment, after the polymerization reaction, the remainder of the catalyst is preferably present in a deactivated form, preferably in a hydrolyzed form, more preferably as $Zn(OH)_2$, $Zn(OH)_4^{2-}$, ZnO or mixtures thereof.

In a preferred embodiment, the polyalkylene oxide contained in the pharmaceutical dosage form according to the invention is obtainable by polymerizing alkylene oxide in presence of the zinc component, preferably of the zinc component according to U.S. Pat. No. 4,667,013 or U.S. Pat. No. 5,326,852 or U.S. Pat. No. 6,979,722 or EP 0 239 973 as described above. In a particularly preferred embodiment, the polyalkylene oxide contained in the pharmaceutical dosage form according to the invention is obtainable by polymerizing alkylene oxide in presence of the zinc component, which is preferably obtainable by reacting a dialkyl zinc with an aliphatic polyhydric alcohol and a monohydric alcohol, as disclosed in U.S. Pat. No. 5,326,852 or U.S. Pat. No. 6,979,722, wherein preferably the amount of the zinc component is in the range of from 0.01 to 1 mol-% based on the zinc atom content per mol of the alkylene oxide monomers.

In a preferred embodiment, the zinc component is the constituent of a polyalkylene oxide composition also comprising the polyalkylene oxide, wherein an aqueous dispersion of the pure polyalkylene oxide composition has a lower pH value than a dispersion of an otherwise comparable polyalkylene oxide not containing the zinc component, typically containing substantially no zinc.

Preferably, the pH value is measured several days after dispersing the pure polyalkylene oxide composition in water, preferably after four days.

In a preferred embodiment, an aqueous dispersion of the pure polyalkylene oxide composition in pure water at 25° C. and at a concentration of 1 wt.-% has a pH value of at most 7.7.

Preferably, an aqueous dispersion of the pure polyalkylene oxide composition in pure water at 25° C. and at a concentration of 1 wt.-% after several days, preferably after four days, has a pH value of at most 7.7. Preferably, an aqueous dispersion of the pure polyalkylene oxide composition in pure water at 25° C. and at a concentration of 1 wt.-% after several days, preferably after four days, has a pH value of at most 7.6, more preferably at most 7.5, still more preferably at most 7.4, yet more preferably at most 7.3, even more preferably at most 7.2, most preferably at most 7.1 and in particular at most 7.0. In still another preferred embodiment, an aqueous dispersion of the pure polyalkylene oxide composition in pure water at 25° C. and at a concentration of 1 wt.-% after several days, preferably after four days, has a pH value of at most 6.9, more preferably at most 6.8 and most preferably at most 6.7.

In a preferred embodiment, the content of the zinc component in the pharmaceutical dosage form according to the invention is at least 1 ppm, more preferably at least 2 ppm, still more preferably at least 5 ppm, yet more preferably at least 7 ppm, even more preferably at least 10 ppm, most preferably at least 15 ppm, and in particular at least at least 20 ppm, relative to the total weight of the pharmaceutical dosage form.

Preferably, the content of the zinc component in the pharmaceutical dosage form according to the invention is below 0.01 g, more preferably below 8 mg and most preferably below 5 mg.

Preferably, the content of the zinc component in the pharmaceutical dosage form according to the invention is at most 10,000 ppm, more preferably at most 8,000 ppm, still more preferably at most 6,000 ppm, yet more preferably at most 5,000 ppm, even more preferably at most 4,000 ppm, most preferably at most 3,000 ppm, and in particular at most 2,000 ppm, relative to the total weight of the pharmaceutical dosage form.

Preferably, the content of the zinc component in the pharmaceutical dosage form according to the invention is at most 1,000 ppm, more preferably at most 950 ppm, still more preferably at most 900 ppm, yet more preferably at most 850 ppm, even more preferably at most 800 ppm, most preferably at most 750 ppm, and in particular at most 700 ppm, relative to the total weight of the pharmaceutical dosage form.

In another preferred embodiment, the content of the zinc component in the pharmaceutical dosage form according to the invention is preferably at most 600 ppm, more preferably at most 400 ppm, still more preferably at most 200 ppm, most preferably at most 100 ppm and in particular at most 80 ppm, relative to the total weight of the pharmaceutical dosage form.

Preferably, the content of the zinc component in the pharmaceutical dosage form according to the invention is below 200 ppm, more preferably below 200 ppm.

For the purpose of specification, unless expressly stated otherwise, "ppm" is to be regarded as ppmw, i.e. parts per million by weight, so that 1 ppm corresponds to 0.0001 wt.-%.

In a preferred embodiment, the pharmaceutical dosage form according to the invention contains a polyalkylene oxide composition that comprises the polyalkylene oxide and the zinc component. According to this embodiment, preferably the content of said zinc component is at least 1 ppm, more preferably at least 2 ppm, still more preferably at least 5 ppm, yet more preferably at least 7 ppm, even more preferably at least 10 ppm, most preferably at least 15 ppm, and in particular at least 20 ppm, relative to the total weight of the polyalkylene oxide composition. Further according to this embodiment, preferably the content of said zinc component is at least 50 ppm, more preferably at least 100 ppm, still more preferably at least 200 ppm, yet more preferably at least 400 ppm, even more preferably at least 600 ppm, most preferably at least 700 ppm, and in particular at least 800 ppm, relative to the total weight of the polyalkylene oxide composition.

In a preferred embodiment, the content of the zinc component in the pharmaceutical dosage form according to the invention is in the range of from 0.01 to 1 mol-%, more preferably 0.015 to 0.5 mol-%, most preferably 0.015 to 0.1 mol-% and in particular 0.018 to 0.05 mol-% based on the zinc atom content per mol of the alkylene oxide units which are contained in the polyalkylene oxide.

In another preferred embodiment, the content of the zinc component in the pharmaceutical dosage form according to the invention amounts to 860±700 ppm, more preferably 860±600 ppm, still more preferably 860±500 ppm, yet more preferably 860±400 ppm, even more preferably 860±300 ppm, most preferably 860±200 ppm and in particular 860±100 ppm, relative to the total weight of the polyalkylene oxide composition.

Preferably, the content of the zinc component in the pharmaceutical dosage form according to the invention is at most 20,000 ppm, more preferably at most 18,000 ppm, most preferably at most 15,000 ppm and in particular at most 12,000 ppm, relative to the total weight of the polyalkylene oxide composition. Preferably, the content of the zinc component in the pharmaceutical dosage form according to the invention is at most 1,000 ppm, more preferably at most 950 ppm, still more preferably at most 900 ppm, yet more preferably at most 850 ppm, even more preferably at most 800 ppm, most preferably at most 750 ppm, and in particular at most 700 ppm, relative to the total weight of the polyalkylene oxide composition. Preferably, the content of the zinc component in the pharmaceutical dosage form according to the invention is at most 600 ppm, more preferably at most 500 ppm, still more preferably at most 400 ppm, yet more preferably at most 300 ppm, most preferably at most 250 ppm and in particular at most 200 ppm, relative to the total weight of the polyalkylene oxide composition.

Preferably, the zinc component is contained in the pharmaceutical dosage form according to the invention in an amount which does not have any physiological effect, in particular adverse effects such as causing emesis. According to this embodiment, the zinc component, preferably zinc sulfate, is preferably contained in the pharmaceutical dosage form according to the invention in an amount of less than 0.01 g, more preferably less than 1 mg, still more preferably less than 0.1 mg, even more preferably less than 0.01 mg, yet more preferably less than 1 µg, most preferably less than 0.1 µg and in particular less than 0.01 µg.

Preferably, the zinc component is contained in the pharmaceutical dosage form according to the invention in an amount which does not have any physiological effect, in particular adverse effects such as causing emesis. According to this embodiment, the zinc component, preferably zinc sulfate, is preferably contained in the pharmaceutical dosage form according to the invention in an amount of less than 10,000 ppm, more preferably less than 1,000 ppm, most preferably less than 500 ppm and in particular less than 100 ppm.

In a preferred embodiment, the zinc component is homogeneously distributed in the pharmaceutical dosage form according to the invention. Preferably, the polyalkylene oxide or the polyalkylene oxide composition and the zinc component are intimately homogeneously distributed in the pharmaceutical dosage form so that the pharmaceutical dosage form does not contain any segments where either zinc component is present in the absence of polyalkylene oxide and polyalkylene oxide composition, respectively, or where the polyalkylene oxide and the polyalkylene oxide composition, respectively, is present in the absence of the zinc component.

When the pharmaceutical dosage form is film coated, the zinc component is preferably homogeneously distributed in the core of the pharmaceutical dosage form, i.e. the film coating preferably does not contain a zinc component.

In a preferred embodiment, the polyalkylene oxide composition according to the invention provides an enhanced shelf life to the pharmaceutical dosage form according to the invention.

In a preferred embodiment, the content of elemental zinc, either in cationic or neutral form, in the pharmaceutical dosage form according to the invention is at least 1 ppm, more preferably at least 2 ppm, still more preferably at least 5 ppm, yet more preferably at least 7 ppm, even more preferably at least 10 ppm, most preferably at least 15 ppm, and in particular at least 20 ppm, relative to the total weight of the pharmaceutical dosage form. In another preferred embodiment, the content of elemental zinc, either in cationic or neutral form, in the pharmaceutical dosage form according to the invention is at least 25 ppm, more preferably at least 35 ppm, still more preferably at least 45 ppm, yet more preferably at least 55 ppm, even more preferably at least 65 ppm, most preferably at least 75 ppm, and in particular at least 85 ppm, relative to the total weight of the pharmaceutical dosage form. In a further preferred embodiment, the content of elemental zinc, either in cationic or neutral form, in the pharmaceutical dosage form according to the invention is at least 100 ppm, more preferably at least 300 ppm, still more preferably at least 500 ppm, yet more preferably at least 800 ppm, even more preferably at least 1,000 ppm, most preferably at least 3,000 ppm, and in particular at least 5,000 or 8,000 ppm, relative to the total weight of the pharmaceutical dosage form.

Particularly preferably, the content of elemental zinc, either in cationic or neutral form, in the pharmaceutical dosage form according to the invention is in the range of from 200 ppm to 800 ppm. In a preferred embodiment, the content of elemental zinc, either in cationic or neutral form, in the pharmaceutical dosage form according to the invention is 250±200 ppm, more preferably 250±150 ppm, still more preferably 250±130 ppm, even more preferably 250±110 ppm, yet more preferably 250±90 ppm, most preferably 250±70 ppm and in particular 250±50 ppm, relative to the total weight of the pharmaceutical dosage form. In another preferred embodiment, the content of elemental zinc, either in cationic or neutral form, in the pharmaceutical dosage form according to the invention is 300±200 ppm, more preferably 300±150 ppm, still more preferably 300±130 ppm, even more preferably 300±110 ppm, yet more preferably 300±90 ppm, most preferably 300±70 ppm and in particular 300±50 ppm, relative to the total weight of the pharmaceutical dosage form. In still another preferred embodiment, the content of elemental zinc, either in cationic or neutral form, in the pharmaceutical dosage form according to the invention is 500±400 ppm, more preferably 500±300 ppm, still more preferably 500±250 ppm, even more preferably 500±200 ppm, yet more preferably 500±150 ppm, most preferably 500±100 ppm and in particular 500±50 ppm, relative to the total weight of the pharmaceutical dosage form. In yet another preferred embodiment, the content of elemental zinc, either in cationic or neutral form, in the pharmaceutical dosage form according to the invention is 700±600 ppm, more preferably 700±500 ppm, still more preferably 700±400 ppm, even more preferably 700±300 ppm, yet more preferably 700±200 ppm, most preferably 700±100 ppm and in particular 700±50 ppm, relative to the total weight of the pharmaceutical dosage form.

Preferably, the content of elemental zinc, either in cationic or neutral form, in the pharmaceutical dosage form according to the invention is at most 2 wt.-%, more preferably at most 1.8 wt.-%, still more preferably at most 1.5 wt.-%, yet more preferably at most 1.3 wt.-%, even more preferably at most 1.0 wt.-% (10,000 ppm), most preferably at most 0.8 wt.-% relative to the total weight of the pharmaceutical dosage form. Preferably, the content of elemental zinc, either in cationic or neutral form, in the pharmaceutical dosage form according to the invention is at most 1,000 ppm, more preferably at most 950 ppm, still more preferably at most 900 ppm, yet more preferably at most 850 ppm, even more preferably at most 800 ppm, most preferably at most 750 ppm, and in particular at most 700 ppm, relative to the total weight of the pharmaceutical dosage form.

Preferably, the content of elemental zinc, either in cationic or neutral form, preferably zinc (II), in the pharmaceutical dosage form according to the invention is in the range of from 0.01 to 1 mol-% based on the zinc atom content per mol of the alkylene oxide units contained in the polyalkylene oxide.

In a preferred embodiment, the content of zinc (II) in the pharmaceutical dosage form according to the invention is at least 0.01 mol-%, more preferably at least 0.03 mol-%, still more preferably at least 0.06 mol-%, yet more preferably at least 0.10 mol-%, even more preferably at least 0.15 mol-%, most preferably at least 0.20 mol-%, and in particular at least 0.5 mol-%, relative to the amount of substance of the pharmacologically active ingredient. In another preferred embodiment, the content of zinc (II) in the pharmaceutical dosage form according to the invention is at least 1 mol-%, more preferably at least 4 mol-%, still more preferably at least 8 mol-%, yet more preferably at least 12 mol-%, even more preferably at least 15 mol-%, most preferably at least 18 mol-%, and in particular at least 20 mol-%, relative to the amount of substance of the pharmacologically active ingredient.

Preferably, the content of zinc (II) in the pharmaceutical dosage form according to the invention is at most 50 mol-%, more preferably at most 45 mol-%, still more preferably at most 40 mol-%, yet more preferably at most 35 mol-%, even more preferably at most 30 mol-%, most preferably at most 25 mol-%, and in particular at most 20 mol-%, relative to the amount of substance of the pharmacologically active ingredient.

In a preferred embodiment, the content of zinc (II) in the pharmaceutical dosage form according to the invention is at least $1 \cdot 10^{-7}$ mol, more preferably at least $2 \cdot 10^{-7}$ mol, still more preferably at least $3 \cdot 10^{-7}$ mol, yet more preferably at least $4 \cdot 10^{-7}$ mol, even more preferably at least $5 \cdot 10^{-7}$ mol, most preferably at least $7 \cdot 10^{-7}$ mol, and in particular at least $1 \cdot 10^{-6}$ mol. In another preferred embodiment, the content of zinc (II) in the pharmaceutical dosage form according to the invention is at least $1 \cdot 10^{-5}$ mol, more preferably at least $1 \cdot 10^{-4}$ mol, still more preferably at least $1 \cdot 10^{-3}$ mol, yet more preferably at least $5 \cdot 10^{-3}$ mol, even more preferably at least $8 \cdot 10^{-3}$ mol, most preferably at least $9 \cdot 10^{-3}$ mol, and in particular at least $1 \cdot 10^{-2}$ mol.

Preferably, the content of zinc (II) in the pharmaceutical dosage form according to the invention is at most $100 \cdot 10^{-3}$ mol, more preferably at most $80 \cdot 10^{-3}$ mol, still more preferably at most $70 \cdot 10^{-3}$ mol, yet more preferably at most $60 \cdot 10^{-3}$ mol, even more preferably at most $50 \cdot 10^{-3}$ mol, most preferably at most $40 \cdot 10^{-3}$ mol, and in particular at most $35 \cdot 10^{-3}$ mol. Preferably, the content of zinc (II) in the pharmaceutical dosage form according to the invention is at most $1 \cdot 10^{-3}$ mol, more preferably at most $7 \cdot 10^{-4}$ mol, still more preferably at most $5 \cdot 10^{-4}$ mol, yet more preferably at most $4 \cdot 10^{-4}$ mol, even more preferably at most $3 \cdot 10^{-4}$ mol, most preferably at most $2 \cdot 10^{-4}$ mol, and in particular at most $1 \cdot 10^{-4}$ mol.

Preferably, the content of the polyalkylene oxide or of the polyalkylene oxide composition is at least 10 wt.-%, more preferably at least 15 wt.-%, still more preferably at least 20 wt.-%, even more preferably at least 25 wt.-%, most preferably at least 30 wt.-% and in particular at least 35 wt.-% based on the total weight of the pharmaceutical dosage form, wherein the content of the zinc component is in the range of from 0.01 to 1 mol-% based on the zinc atom content per mol of the alkylene oxide units contained in the polyalkylene oxide.

Preferably, the content of the polyalkylene oxide or of the polyalkylene oxide composition is within the range of from 20 to 99 wt.-%, more preferably 25 to 95 wt.-%, still more preferably 30 to 90 wt.-%, yet more preferably 30 to 85 wt.-%, most preferably 30 to 80 wt.-% and in particular 30 to 75 wt.-% or 45 to 70 wt.-%, based on the total weight of the pharmaceutical dosage form. The content of the polyalkylene oxide or of the polyalkylene oxide composition is at least 20 wt.-%, preferably at least 25 wt.-%, more preferably at least 30 wt.-%, still more preferably at least 35 wt.-% and in particular at least 40 wt.-%, based on the total weight of the pharmaceutical dosage form.

In a preferred embodiment, the overall content of the polyalkylene oxide or of the polyalkylene oxide composition is within the range of 25±5 wt.-%. In another preferred embodiment, the overall content of the polyalkylene oxide or of the polyalkylene oxide composition is within the range of 35±15 wt.-%, more preferably 35±10 wt.-%, and in particular 35±5 wt.-%. In still another preferred embodiment, the overall content of the polyalkylene oxide or of the polyalkylene oxide composition is within the range of 45±20 wt.-%, more preferably 45±15 wt.-%, most preferably 45±10 wt.-%, and in particular 45±5 wt.-%. In yet another preferred embodiment, the overall content of the polyalkylene oxide or of the polyalkylene oxide composition is within the range of 55±20 wt.-%, more preferably 55±15 wt.-%, most preferably 55±10 wt.-%, and in particular 55±5 wt.-%. In a further preferred embodiment, the overall content of the polyalkylene oxide or of the polyalkylene oxide composition is within the range of 65±20 wt.-%, more preferably 65±15 wt.-%, most preferably 65±10 wt.-%, and in particular 65±5 wt.-%. In still a further a preferred embodiment, the overall content of the polyalkylene oxide or of the polyalkylene oxide composition is within the range of 75±20 wt.-%, more preferably 75±15 wt.-%, most preferably 75±10 wt.-%, and in particular 75±5 wt.-%. In yet a further a preferred embodiment, the overall content of the polyalkylene oxide or of the polyalkylene oxide composition is within the range of 80±15 wt.-%, more preferably 80±10 wt.-%, and most preferably 80±5 wt.-%.

In a preferred embodiment, the polyalkylene oxide or the polyalkylene oxide composition is homogeneously distributed in the pharmaceutical dosage form according to the invention. Preferably, the pharmacologically active ingredient and the polyalkylene oxide or the polyalkylene oxide composition are intimately homogeneously distributed in the pharmaceutical dosage form so that the pharmaceutical dosage form does not contain any segments where either pharmacologically active ingredient is present in the absence of polyalkylene oxide and polyalkylene oxide composition, respectively, or where the polyalkylene oxide and the polyalkylene oxide composition, respectively, is present in the absence of the pharmacologically active ingredient.

When the pharmaceutical dosage form is film coated, the polyalkylene oxide or the polyalkylene oxide composition is preferably homogeneously distributed in the core of the pharmaceutical dosage form, i.e. the film coating preferably does not contain polyalkylene oxide or polyalkylene oxide composition. Nonetheless, the film coating as such may of course contain one or more polymers, which however, preferably differ from the polyalkylene oxide or polyalkylene oxide composition contained in the core.

The polyalkylene oxide may be combined with or the polyalkylene oxide composition may additionally comprise one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinyl-pyrrolidone, poly(alk)acrylate, poly (hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), hydroxypropyl methylcellulose (Hypromellose); polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, the relative weight ratio of the polyalkylene oxide or polyalkylene oxide composition to the pharmacologically active ingredient is at least 0.5:1, more preferably at least 1:1, at least 2:1, at least 3:1, at least 4:1, at least 5:1, at least 6:1, at least 7:1, at least 8:1 or at least 9:1; still more preferably at least 10:1 or at least 15:1, yet more preferably at least 20:1, most preferably at least 30:1 and in particular at least 40:1. In a preferred embodiment, the relative weight ratio of the polyalkylene oxide or polyalkylene oxide composition to the pharmacologically active ingredient is within the range of from 3:1 to 50:1, more preferably 3:1 to 40:1 and in particular 3:1 to 30:1.

In a preferred embodiment, the polyalkylene oxide composition according to the invention provides an enhanced stability to the pharmacologically active ingredient.

Besides the pharmacologically active ingredient and the polyalkylene oxide or the polyalkylene oxide composition, the pharmaceutical dosage form according to the invention may contain further ingredients, e.g. one or more conventional pharmaceutical excipient(s), e.g. inorganic salts, fillers, glidants, binding agents, granulating agents, anti-caking agents, lubricants, flavours, dyes, and/or preservatives.

Preferably, the pharmaceutical dosage form according to the invention does not contain a zinc component as a lubricant or glidant. More preferably, the pharmaceutical dosage form according to the invention contains substantially no zinc stearate as a lubricant or glidant which is particularly used to obtain desired flow and less friction during compressing operation.

In a preferred embodiment, the pharmaceutical dosage form according to the invention contains at most 1,000 ppm, more preferably at most 500 ppm, still more preferably at most 100 ppm, even more preferably at most 10 ppm, yet more preferably at most 1 ppm, most preferably at most 0.1 ppm and in particular at most 0.01 ppm of a calcium component. In a particularly preferred embodiment, the pharmaceutical dosage form according to the invention contains substantially no calcium component.

Preferably, the pharmaceutical dosage form comprises a plasticizer. The plasticizer improves the processability of the polyalkylene oxide or polyalkylene oxide composition. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.1 to 25 wt.-%, more preferably 0.5 to 22.5 wt.-%, still more preferably 1.0 to 20 wt.-%, yet more preferably 2.5 to 17.5 wt.-%, most preferably 5.0 to 15 wt.-% and in particular 7.5 to 12.5 wt.-%, based on the total weight of the pharmaceutical dosage form.

In a preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the plasticizer is a polyalkylene glycol having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

In a preferred embodiment, the relative weight ratio of the polyalkylene oxide or polyalkylene oxide composition to the optionally contained polyalkylene glycol is within the range of 4.2±2:1, more preferably 4.2±1.5:1, still more preferably 4.2±1:1, yet more preferably 4.2±0.5:1, most preferably 4.2±0.2:1, and in particular 4.2±0.1:1. This ratio satisfies the requirements of relative high polyalkylene oxide content and good extrudability.

When manufacturing the pharmaceutical dosage forms from slices that are obtained by cutting an extrudate strand, the weight of the slices determines the weight of the resulting dosage form. Pronounced variation in weight of these slices results in an accordant weight deviation of dosage forms from the target weight. The weight variation of slices depends strongly on the surface properties of the extrudate strand. A strand with a thoroughly smooth surface allows the generation of slices exhibiting a low weight variation. In contrast, a wavy or shark skinned strand results in slices exhibiting a higher weight variation thereby increasing the number of rejects.

In a preferred embodiment, the surface properties of the extrudate strand can be triggered by the polyalkylene oxide: polyalkylene glycol weight ratio.

Preferably, the pharmaceutical dosage form further comprises an anti-oxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably used in quantities of 0.01 to 10 wt.-%, preferably of 0.03 to 5 wt.-%, relative to the total weight of the pharmaceutical dosage form.

In a preferred embodiment, the pharmaceutical dosage form further comprises an acid, preferably citric acid. The amount of acid is preferably in the range of 0.01 to about 20 wt.-%, more preferably in the range of 0.02 to about 10 wt.-%, and most preferably in the range of 0.05 to about 5 wt.-% relative to the total weight of the pharmaceutical dosage form.

In a preferred embodiment, the pharmaceutical dosage form contains a natural, semi-synthetic or synthetic wax. Waxes with a softening point of at least 50° C., more preferably 60° C. are preferred. Carnauba wax and beeswax are particularly preferred, especially carnauba wax.

In a preferred embodiment, the pharmaceutical dosage form further comprises another polymer which is preferably selected from cellulose esters and cellulose ethers, in particular hydroxypropyl methylcellulose (HPMC). The amount of the further polymer, preferably hydroxypropyl methylcellulose, preferably ranges from 0.1 wt.-% to about 30 wt.-%, more preferably in the range of 1.0 wt.-% to about 20 wt.-%, and most preferably in the range of 2.0 wt.-% to about 15 wt.-% relative to the total weight of the pharmaceutical dosage form.

In another preferred embodiment, the pharmaceutical dosage form according to the invention does not contain any further polymer besides the polyalkylene oxide or polyalkylene oxide composition and optionally, the polyethylene glycol.

The pharmaceutical dosage form according to the invention is preferably an oral dosage form, particularly a tablet. It is also possible, however, to administer the pharmaceutical dosage form via different routes and thus, the pharmaceutical dosage form may alternatively be adapted for buccal, lingual, rectal or vaginal administration. Implants are also possible.

In a preferred embodiment, the pharmaceutical dosage form according to the invention is monolithic or multiparticulate.

In a preferred embodiment, the pharmaceutical dosage form according to the invention is monolithic.

Preferably, the pharmaceutical dosage form is neither in film form, nor multiparticulate.

In a preferred embodiment, the pharmaceutical dosage form according to the invention is a round tablet. Tablets of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is an oblong tablet. Tablets of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

The pharmaceutical dosage form according to the invention has preferably a weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.25 g to 0.8 g.

The pharmaceutical dosage form according to the invention is prepared by thermoforming.

Preferably, the pharmaceutical dosage form according to the invention is prepared by hot-melt extrusion, although also other methods of thermoforming may be used in order to manufacture the pharmaceutical dosage form according to the invention such as press-molding at elevated temperature or heating of tablets that were manufactured by conventional compression in a first step and then heated above the softening temperature of the polymer in the tablet in a second step to form hard tablets. In this regards, thermoforming means the forming or molding of a mass after the application of heat. In a preferred embodiment, the pharmaceutical dosage form is thermoformed by hot-melt extrusion.

In a preferred embodiment, the pharmaceutical dosage form is prepared by hot melt-extrusion, preferably by means of a twin-screw-extruder. Melt extrusion preferably provides a melt-extruded strand that is preferably cut into monoliths, which are then compressed and formed into tablets. In this regard, the term "tablets" is preferably not to be understood as dosage forms being made by compression of powder or granules (compressi) but rather, as shaped extrudates. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air. Alternatively, the shaping can take place as described in EP-A 240 906 by the extrudate being passed between two counter-rotating calender rolls and being shaped directly to tablets. It is of course also possible to subject the extruded strands to the compression step or to the cutting step when still warm, that is more or less immediately after the extrusion step. The extrusion is preferably carried out by means of a twin-screw extruder.

The pharmaceutical dosage form of the invention can optionally be provided, partially or completely, with a conventional coating. The pharmaceutical dosage forms of the present invention are preferably film coated with conventional film coating compositions. Particularly preferably, the pharmaceutical dosage forms according to the invention are either not coated at all or completely coated, but preferably not partially coated.

Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinylacetate; and natural film formers, such as shellack.

In a particularly preferred embodiment, the coating is water-soluble. In a preferred embodiment, the coating is based on polyvinyl alcohol, such as polyvinyl alcohol-part. Hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPa·s.

The coating can be resistant to gastric juices and dissolve as a function of the pH value of the release environment. By means of this coating, it is possible to ensure that the pharmaceutical dosage form according to the invention passes through the stomach undissolved and the pharmacologically active ingredient is only released in the intestines. The coating which is resistant to gastric juices preferably dissolves at a pH value of between 5 and 7.5. Corresponding materials and methods for the delayed release of pharmacologically active ingredients and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

The coating can also be applied e.g. to improve the aesthetic impression and/or the taste of the pharmaceutical dosage forms and the ease with which they can be swallowed. Coating the pharmaceutical dosage forms of the present invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Optionally, the coating can contain a therapeutically effective amount of one or more pharmacologically active ingredients to provide for an immediate release of said pharmacologically active ingredient and thus for an immediate relief of the symptoms treated by said pharmacologically active ingredient. Coated dosage forms of the present invention are preferably prepared by first making the cores and subsequently coating said cores using conventional techniques, such as coating in a coating pan.

In a preferred embodiment, the pharmaceutical dosage form according to the invention provides immediate release of the pharmacologically active ingredient contained therein.

In another preferred embodiment, the pharmaceutical dosage form according to the invention contains the pharmacologically active ingredient in a controlled-release matrix that provides controlled release of the pharmacologically active ingredient contained therein.

The controlled release of the pharmaceutical dosage form according to the invention preferably does not rely on a coating that remains intact during the release phase and covers the matrix composition in such a manner that only a specific surface area is subject to erosion. Thus, the surface area of the pharmaceutical dosage form according to the invention from which the active substance is released is preferably not kept substantially constant by means of such a coating. On the contrary, the controlled release of the pharmaceutical dosage form according to the invention is preferably based on the properties of the matrix in which the pharmacologically active ingredient is embedded so that inert coatings can be completely omitted. Thus, while the pharmaceutical dosage form according to the invention may be coated with conventional coating materials such as polyvinyl alcohol, it is preferably not coated with inert coating materials that serve the purpose of permanently covering a substantial portion of the outer surface of the pharmaceutical dosage form in order to allow drug release only through a predetermined, uncoated portion. Thus, in a preferred embodiment, the pharmaceutical dosage form according to the invention is uncoated, or it is coated with a coating material that substantially covers the complete outer surface of the pharmaceutical dosage form, but does not leave a certain portion uncoated.

In a preferred embodiment, the pharmacologically active ingredient is embedded in a controlled-release matrix comprising the polyalkylene oxide and the zinc component, preferably of the polyalkylene oxide composition that is composed of the polyalkylene oxide and the zinc component.

Controlled release of an pharmacologically active ingredient from an oral dosage form is known to a person skilled in the art. For the purpose of specification, controlled release encompasses delayed release, retarded release, sustained release, extended release, prolonged release, and the like.

Controlled or prolonged release is understood according to the invention preferably to mean a release profile in which the pharmacologically active ingredient is released over a relatively long period with reduced intake frequency with the purpose of extended therapeutic action. Preferably, the meaning of the term "prolonged release" is in accordance with the European guideline on the nomenclature of the release profile of pharmaceutical dosage forms (CHMP). This is achieved in particular with peroral administration. The expression "at least partially delayed or prolonged release" covers according to the invention any pharmaceutical dosage forms which ensure modified release of the pharmacologically active ingredient contained therein. The pharmaceutical dosage forms preferably comprise coated or uncoated pharmaceutical dosage forms, which are produced with specific auxiliary substances, by particular processes or by a combination of the two possible options in order to purposefully change the release rate or location of release.

In the case of the pharmaceutical dosage forms according to the invention, the release time profile of a controlled-release form may be modified e.g. as follows: extended release, repeat action release, prolonged release and sustained release.

For the purpose of specification, "controlled release" preferably means a product in which the release of pharmacologically active ingredient over time is controlled by the type and composition of the formulation. For the purpose of specification "extended release" preferably means a product in which the release of pharmacologically active ingredient is delayed for a finite lag time, after which release is unhindered. For the purpose of specification "repeat action release" preferably means a product in which a first portion of pharmacologically active ingredient is released initially, followed by at least one further portion of pharmacologically active ingredient being released subsequently. For the purpose of specification "prolonged release" preferably means a product in which the rate of release of pharmacologically active ingredient from the formulation after administration has been reduced over time, in order to maintain therapeutic activity, to reduce toxic effects, or for some other therapeutic purpose. For the purpose of specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and Eur. Ph.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active ingredient. Further preferred release profiles $R_1$ to $R_6$ are summarized in the table here below [all data in wt.-% of released pharmacologically active ingredient]:

| time | $R_1$ | $R_2$ | $R_3$ | $R_4$ | $R_5$ | $R_6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1,440 min | 50-100 | 50-100 | >90 | | | |
| 2,160 min | >80 | >80 | | | | |

Further preferred release profiles $R_1$ to $R_6$ are summarized in the table here below [all data in wt.-% of released pharmacologically active ingredient]:

| time | $R_7$ | $R_8$ | $R_9$ | $R_{10}$ | $R_{11}$ | $R_{12}$ |
|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 |
| 60 min | 27.0 ± 8.0 | 27.0 ± 7.0 | 27.0 ± 6.0 | 27.0 ± 5.0 | 27.0 ± 4.0 | 27.0 ± 3.0 |
| 120 min | 41.5 ± 9.5 | 41.5 ± 8.5 | 41.5 ± 7.5 | 41.5 ± 6.5 | 41.5 ± 5.5 | 41.5 ± 4.5 |
| 240 min | 64.5 ± 12.5 | 64.5 ± 11.5 | 64.5 ± 10.5 | 64.5 ± 9.5 | 64.5 ± 8.5 | 64.5 ± 7.5 |
| 480 min | 88.0 ± 12.0 | 88.0 ± 11.0 | 88.0 ± 10.0 | 88.0 ± 9.0 | 88.0 ± 8.0 | 88.0 ± 7.0 |
| 720 min | 96.0 ± 9.0 | 96.0 ± 8.0 | 96.0 ± 7.0 | 96.0 ± 6.0 | 96.0 ± 5.0 | 96.0 ± 4.0 |
| 840 min | 97.5 ± 7.5 | 97.5 ± 6.5 | 97.5 ± 5.5 | 97.5 ± 4.5 | 97.5 ± 3.5 | 97.5 ± 2.5 |

Preferably, the release profile of the pharmaceutical dosage form according to the invention is stable upon storage, preferably upon storage at elevated temperature, e.g. 40° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active ingredient that was originally contained in the pharmaceutical dosage form.

Suitable in vitro conditions are known to the skilled artisan. In this regard it can be referred to, e.g., the Eur. Ph. Preferably, the release profile is measured under the following conditions: Paddle apparatus equipped with sinker, 75 rpm, 37±5° C., 600 mL simulated intestinal fluid pH 6.8 (phosphate buffer) or pH 4.5. In a preferred embodiment, the rotational speed of the paddle is increased to 100 rpm.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of specification, "twice daily" means equal or nearly equal time intervals, i.e., about every 12 hours, or different time intervals, e.g., 8 and 16 hours or 10 and 14 hours, between the individual administrations.

For the purpose of specification, "thrice daily" means equal or nearly equal time intervals, i.e., about every 8 hours, or different time intervals, e.g., 6, 6 and 12 hours; or 7, 7 and 10 hours, between the individual administrations.

A skilled person is fully aware that the above administration regimens twice daily or thrice daily, respectively, require an adaption of the dose of the pharmacologically active ingredient contained in the pharmaceutical dosage forms so that the total administered daily dose of the pharmacologically active ingredient, i.e. the sum of the doses contained in two or three, respectively, adapted pharmaceutical dosage forms, does not exceed the dose of the pharmacologically active ingredient contained in the dosage form which is adapted for administration once daily.

Preferably, the pharmaceutical dosage form according to the invention releases after 5 h at most 99%, more preferably at most 90%, still more preferably at most 75%, and most preferably at most 60% of the pharmacologically active ingredient.

In a particular preferred embodiment,
- the thermoformed pharmaceutical dosage form is prepared by hot melt-extrusion; and/or
- the pharmaceutical dosage form exhibits a breaking strength of at least 300 N; and/or the pharmaceutical dosage form is adapted for administration once daily, twice daily or thrice daily; and/or the pharmacologically active ingredient is selected from the group of opioids and opioid derivatives; and/or the polyalkylene oxide is selected from polymethylene oxide, polyethylene oxide and polypropylene oxide, or copolymers or mixtures thereof; having a weight average molecular weight ($M_W$) of more than 200,000 g/mol, preferably of at least 500,000 g/mol, more preferably within the range of from 1,000,000 g/mol to 10,000,000 g/mol; and/or the pharmaceutical dosage form contains a polyalkylene oxide composition including the polyalkylene oxide and the zinc component; and/or the content of said zinc component is at least 1 ppm and at most 10,000 ppm relative to the total weight of the pharmaceutical dosage form; and/or the content of the zinc component in the pharmaceutical dosage form is in the range of from 0.01 to 1 mol-% based on the zinc atom content per mol of the alkylene oxide units contained in the polyalkylene oxide; and/or the polyalkylene oxide is obtainable by polymerizing alkylene oxide in presence of the zinc component; and/or the polyalkylene oxide is obtainable by polymerizing alkylene oxide in presence of the zinc component, wherein the amount of said zinc component is in the range of from 0.01 to 1 mol-% based on the zinc atom content per mol of alkylene oxide; and/or an aqueous dispersion of the pure polyalkylene oxide composition according to the invention containing the zinc component in pure water having a pH value that is lower than the dispersion of a polyalkylene oxide containing substantially no zinc; and/or the content of the polyalkylene oxide or of the polyalkylene oxide composition is at least 30 wt.-%, based on the total weight of the pharmaceutical dosage form.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding pharmacologically active ingredient, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance pharmacologically active ingredient. Corresponding hot substance pharmacologically active ingredients are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredient, preferably no antagonists against psychotropic substances, in particular no antagonists against opioids. Antagonists suitable for a given pharmacologically active ingredient are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure. The pharmaceutical dosage form according to the invention preferably also contains no apomorphine as an emetic. Preferably, the pharmaceutical dosage form according to the invention does not contain a zinc component as an emetic. Particularly preferably, the pharmaceutical dosage form according to the invention does not contain zinc sulfate, which is useful as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredient, nor emetics, nor bitter substances.

The pharmaceutical dosage form according to the invention is tamper resistant. Preferably, tamper-resistance is achieved based on the mechanical properties of the pharmaceutical dosage form so that comminution is avoided or at least substantially impeded. The pharmaceutical dosage form according to the invention preferably has a breaking strength of at least 300 N. According to the invention, the term comminution means the pulverization of the pharmaceutical dosage form using conventional means usually available to an abuser, for example a pestle and mortar, a hammer, a mallet or other conventional means for pulverizing under the action of force. Thus, tamper-resistance preferably means that pulverization of the pharmaceutical dosage form using conventional means is avoided or at least substantially impeded.

Preferably, the mechanical properties of the pharmaceutical dosage form according to the invention, particularly its breaking strength, substantially rely on the presence and spatial distribution of the polyalkylene oxide and of the polyalkylene oxide composition, respectively, although their mere presence does typically not suffice in order to achieve said properties. The advantageous mechanical properties of the pharmaceutical dosage form according to the invention may not automatically be achieved by simply processing pharmacologically active ingredient, polyalkylene oxide, a zinc component, and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the pharmaceutical dosage forms exhibiting the desired properties may be obtained only if, during preparation of the pharmaceutical dosage form,
  suitable components
  in suitable amounts
are exposed to
  sufficient pressure
  at sufficient temperature
  for a sufficient period of time.

Thus, regardless of the apparatus used, the process protocols must be adapted in order to meet the required criteria. Therefore, the breaking strength is separable from the composition.

The pharmaceutical dosage form according to the invention preferably has a breaking strength of at least 300 N, preferably at least 400 N, more preferably at least 500 N, still more preferably at least 600 N, yet more preferably at least 700 N, even more preferably at least 800 N most preferably at least 900 N and in particular at least 1,000 N. In another preferred embodiment, the pharmaceutical dosage form according to the invention has a breaking strength of at least 1,100 N, preferably at least 1,200 N, more preferably at least 1,300 N, most preferably at least 1,400 N and in particular at least 1,500 N.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of specification, the breaking strength is preferably defined as the amount of force that is necessary in order to fracture the pharmaceutical dosage form (=breaking force). Therefore, for the purpose of specification the pharmaceutical dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The pharmaceutical dosage forms according to the invention are distinguished from conventional pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active ingredient in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 300 N would require a diameter of at least 30 mm). Such a tablet, however, could not be swallowed. The above empirical formula preferably does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468). This means that conventional tablets having a breaking strength well below 200 N may be crushed upon spontaneous chewing, whereas the pharmaceutical dosage forms according to the invention may not.

Still further, when applying a gravitational acceleration of about 9.81 m/s$^2$, 300 N correspond to a gravitational force of more than 30 kg, i.e. the pharmaceutical dosage forms according to the invention can preferably withstand a weight of more than 30 kg without being pulverized.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2005/016313, WO 2005/016314, and WO 2006/082099, which can be regarded as a modification of the method described in the Eur. Ph. The apparatus used for the measurement is preferably a "Zwick Z 2.5" materials tester, $F_{max}$=2.5 kN with a maximum draw of 1,150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centering device.

In a preferred embodiment of the invention, the breaking strength is measured by means of a breaking strength tester e.g. Sotax®, type HT100 or type HT1 (Allschwil, Switzerland). Both, the Sotax® HT100 and the Sotax® HT1 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the pharmaceutical dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed, e.g. plastically, when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break (plastic deformation or plastic flow) is preferably to be regarded as having the desired breaking strength in said direction of extension.

In a preferred embodiment, the invention relates to a tamper-resistant pharmaceutical dosage form having a retarded release profile, especially a tamper-resistant oral dosage form having a retarded release profile, particularly a tamper-resistant tablet having a retarded release profile comprising at least one pharmaceutically pharmacologically active ingredient (pharmacologically active compound) with potential for abuse.

The pharmaceutical dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

The present invention also relates to pharmaceutical dosage forms that are obtainable by any of the processes described here below.

In a preferred embodiment, the pharmaceutical dosage form is manufactured in a process comprising the steps of
(a) mixing a pharmacologically active ingredient, a polyalkylene oxide composition comprising a polyalkylene oxide having a weight average molecular weight of more than 200,000 g/mol and a zinc component, and optionally present excipients, wherein the content of the zinc component is at least 1 ppm, relative to the total weight of the mixture prepared in step (a);
(b) press-forming the mixture obtained in step (a) with preceding, simultaneous, or subsequent exposure to heat.

In general, the process for the production of the pharmaceutical dosage form according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide up to its softening point;
(c) hardening the mixture by applying heat and force, it being possible to supply the heat during and/or before the application of force and the quantity of heat supplied being sufficient to heat the polyalkylene oxide at least up to its softening point;

(d) optionally singulating the hardened mixture;
(e) optionally shaping the pharmaceutical dosage form; and
(f) optionally providing a film coating.

Heat may be supplied directly, e.g. by contact or by means of hot gas such as hot air, or with the assistance of ultrasound. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

Preferably, hot-melt extrusion is performed in the absence of additional water.

The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide. However, extrusion at lower temperatures, e.g. ambient temperature, is also possible and may be preferred.

Shaping can be performed, e.g., by means of a tabletting press comprising die and punches of appropriate shape.

A particularly preferred process for the manufacture of the pharmaceutical dosage form of the invention involves hot-melt extrusion. In this process, the pharmaceutical dosage form according to the invention is produced by thermoforming with the assistance of an extruder, preferably without there being any observable consequent discoloration of the extrudate.

This process is characterized in that
a) all components are mixed,
b) the resultant mixture is heated in the extruder at least up to the softening point of the polyalkylene oxide and extruded through the outlet orifice of the extruder by application of force,
c) the still plastic extrudate is singulated and formed into the pharmaceutical dosage form or
d) the cooled and optionally reheated singulated extrudate is formed into the pharmaceutical dosage form.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The preferably molten mixture which has been heated in the extruder at least up to the softening point of the polyalkylene oxide is extruded from the extruder through a die with at least one bore.

The extrusion process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 30%, i.e. that when using a die with a bore having a diameter of e.g. 6 mm, the extruded strand should have a diameter of not more than 8 mm. More preferably, the expansion of the strand is not more than 25%, still more preferably not more than 20%, most preferably not more than 15% and in particular not more than 10%.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide proceeding in the first zone, which is downstream from a feed zone and optionally mixing zone. The throughput of the mixture is preferably from 1.0 kg to 30 kg/hour, more preferably 1.0 kg to 15 kg/hour. In a preferred embodiment, the throughput is from 1 to 3.5 kg/hour. In another preferred embodiment, the throughput is from 4 to 15 kg/hour.

In a preferred embodiment, the die head pressure is within the range of from 25 to 200 bar, more preferably 25 to 100 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide and does not rise above a temperature at which the pharmacologically active ingredient to be processed may be damaged. Preferably, the temperature of the mixture to be extruded is adjusted to below 180° C., preferably below 150° C., but at least to the softening temperature of the polyalkylene oxide. Typical extrusion temperatures are 120° C. and 130° C.

In a preferred embodiment, the extruder torque is within the range of from 30 to 95%. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

Preferably, intermediate or final storage of the optionally singulated extrudate or the final shape of the pharmaceutical dosage form according to the invention is performed under oxygen-free atmosphere which may be achieved, e.g., by means of oxygen-scavengers.

The singulated extrudate may be press-formed into tablets in order to impart the final shape to the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nürnberg, Germany), screw diameters of 18 or 27 mm. Screws having eccentric ends may be used. A heatable die with a round bore having a diameter of 7, 8, or 9 mm may be used. The extrusion parameters may be adjusted e.g. to the following values: rotational speed of the screws: 120 Upm; delivery rate 2 kg/h for a ZSE 18 or 8 kg/h for a ZSE27; product temperature: in front of die 125° C. and behind die 135° C.; and jacket temperature: 110° C. In another preferred embodiment, extrusion is performed by means of a twin-screw-extruder, type ZSE 27 PH 40 D (Leistritz, Nürnberg, Germany), with a diameter of the extrusion die of 5.5 mm or 7 mm at a temperature of the extrusion die of 135° C.).

Preferably, extrusion is performed by means of twin-screw-extruders or planetary-gear-extruders, twin-screw extruders (co-rotating or contra-rotating) being particularly preferred.

The pharmaceutical dosage form according to the invention is preferably produced by thermoforming with the assistance of an extruder without any observable consequent discoloration of the extrudates.

The process for the preparation of the pharmaceutical dosage form according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the pharmacologically active ingredient, uniform mechanical properties, uniform porosity, uniform appearance of the surface, etc. Only under these circumstances the uniformity of the pharmacological properties, such as the stability of the release profile, may be ensured and the amount of rejects can be kept low.

A further aspect of the invention relates to the use of a pharmacologically active ingredient for the manufacture of the pharmaceutical dosage form as described above for the treatment of pain.

A further aspect of the invention relates to the use of a pharmaceutical dosage form as described above for avoiding or hindering the abuse of the pharmacologically active ingredient contained therein.

A further aspect of the invention relates to the use of a pharmaceutical dosage form as described above for avoiding or hindering the unintentional overdose of the pharmacologically active ingredient contained therein.

In this regard, the invention also relates to the use of a pharmacologically active ingredient as described above and a polyalkylene oxide composition as described above for the manufacture of the pharmaceutical dosage form according to the invention for the prophylaxis and/or the treatment of a disorder, thereby preventing an overdose of the pharmacologically active ingredient, particularly due to comminution of the pharmaceutical dosage form by mechanical action.

Further, the invention relates to a method for the prophylaxis and/or the treatment of a disorder comprising the administration of the pharmaceutical dosage form according to the invention, while at the same time preventing an overdose of the pharmacologically active ingredient, particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The following examples further illustrate the invention but are not to be construed as limiting its scope:

EXAMPLE 1

Four samples containing different types of polyethylene oxides were prepared by dispersing the polyethylene oxide (1.0 g) in water (99.0 g) using an IKA Ultra-Turrax T-25 disperser. Afterwards, the dispersion was stirred for 1 h using an IKA RCT basic safety control magnetic stirrer. When using PEO 20NF, PEO 18NF and PEO Coagulant, dispersion was repeated followed by stirring for 15 min. After four days, gel formation was complete and the pH values were measured using a Knick type 765 laboratory pH meter. All measurements were conducted at 25° C. The pH values of the different samples are summarized in the following table:

| | polyethylene oxide product | $M_w$ [g · mol$^{-1}$] | viscosity [mPa · s] | pH |
|---|---|---|---|---|
| inventive | PEO 18NF | 4,500,000 | 5,500-7,500 | 6.31 |
| | PEO 20NF | 5,000,000 | 7,500-10,000 | 6.41 |
| comparative | Polyox ® Coagulant | 5,000,000 | 5,500-6,280 | 7.78 |
| | Polyox ® WSR303 | 7,000,000 | 7,500-10,000 | 8.25 |

The aqueous dispersions of polyethylene oxides PEO 20NF and PEO 18NF (commercialized by Sumitomo) had pH values of 6.41 and 6.31, respectively. According to the product specification, zinc was present at a zinc content below 1,000 ppm.

The pH values of the comparative examples Polyox® WSR303 and Polyox® Coagulant (commercialized by Dow) amounted to 8.25 and 7.78, respectively. According to the manufacturer, zinc is not used in any part of the Polyox® WSR301 manufacturing process and although not specifically tested, it is not expected to be present. Polyox® WSR301 is a homologue of Polyox® WSR303.

EXAMPLE 2

A stability study was conducted comparing pharmaceutical dosage forms manufactured at commercial scale (batch sizes 15 kg or 85 kg) using polyethylene oxide containing zinc (inventive examples) or zinc-free polyethylene oxide (comparative examples). All tablets had a high breaking strength of above 500 N.

Two different formulations were prepared, containing 56.29 wt.-% and 35.00 wt.-% of polyethylene oxide (zinc containing or zinc free), respectively.

The zinc-containing polyethylene oxide was PEO 20NF (7,500-10,000 mPa·s) of Sumitomo and is referred to in the following as "PEO, Zn containing". The zinc-free polyethylene oxide was Polyox® WSR303 (7,500-10,000 mPa·s) of Dow and is referred to in the following as "PEO, Zn free".

In order to exclude batch-specific differences, each formulation was prepared at least twice by using the same type of chemical compounds in the same amounts only partially differing in the commercially available batches, i.e. lot numbers.

According to the manufacturer's certificates of analysis, the Zn content in the zinc-containing polyethylene oxide batches was about 0.086%.

The mixtures of the pharmacologically active ingredient, polyalkylene oxide and excipients were extruded by means of a twin-screw-extruder (type ZSE 27 PH 40 D, diameter of extrusion die 5.5 mm for the compositions I/C 1-x and 7 mm for the compositions I/C 2-x, temperature of extrusion die 135° C.).

Details on the formulations tested can be found in the following table:

| | 1: amount in % up to 103% with tablet core equaling 100% (amount per tablet in mg with total weight of tablet of 412.00 mg) | | | | | | | |
|---|---|---|---|---|---|---|---|---|
| | PEO Zn containing | PEO Zn free | Tapentadol-HCl | Hypromellose 100000 mPas, Ph. Eur. | Macrogol 6000, Ph. Eur. | α-Tocopherol | PEG | Opadry ® II white 85F18422 |
| I 1-1 and I 1-2 | 56.29 (225.16) | — | 14.56 (58.24) | 14.00 (56.00) | 14.08 (56.31) | 0.15 (0.60) | 0.92 (3.69) | 3.00 (12.00) |
| C 1-1, C 1-2, C 1-3 and C 1-4 | — | 56.29 (225.16) | | | | | | |

| | 2: amount in % up to 103% with tablet core equaling 100% (amount per tablet in mg with total weight of tablet of 721.00 mg) | | | | | | | |
|---|---|---|---|---|---|---|---|---|
| | PEO Zn containing | PEO Zn free | Tapentadol-HCl | Hypromellose 100000 mPas, Ph. Eur. | Macrogol 6000, Ph. Eur. | α-Tocopherol | PEG | Opadry ® II red 85F35244 |
| I 2-1 and I 2-2 | 35.00 (245.00) | — | 41.60 (291.20) | 14.00 (98.00) | 8.69 (60.80) | 0.10 (0.70) | 0.61 (4.30) | 3.00 (21.00) |
| C 2-1, C 2-2, C 2-3 and C 2-4 | — | 35.00 (245.00) | | | | | | |

The film-coated tablets were packaged into blisters and put on stability. Storage conditions were 25° C./60% r.h., 30° C./75% r.h., and 40° C./75% r.h.

As indicative parameters for the degradation of polyethylene oxide viscosity and α-tocopherol consumption were identified. When the polymer chains detoriate, the viscosity of the aqueous gel of the tablet decreases. The degradation of polyethylene oxide is an oxidative process, therefore it is linked to a decrease in the content of the antioxidant α-tocopherol in the formulation.

In particular, the beneficial effects of the zinc containing dosage forms according to the invention become evident at the harsher storage conditions (40° C./75% r.h.).

After storage for 6 months at 40° C./75% r.h., the tablets still had a high breaking strength of above 500 N.

Description of the Method for Determining the Viscosity:

One or two tablets are cut into smaller pieces and accurately weighed (242+/−3 mg for I/C 1-x, 388+/−3 mg for I/C 2-x) and dissolved in 2 mL 2-Propanole and 10 mL water. Dissolving takes place over 72 hours while shaking on a mechanical agitator at 175 to 250 rpm. 2 mL of the formed solution are measured in the viscosimeter.

Apparatus: Thermo Scientific HAAKE RotoViscol, equipped with a RV1 plate system and a C60/1° cone with a split of 0.052 mm. Temperature is 25.0° C.+/−0.1° C. The measurement takes place in CR mode, starting at a shear rate of 0.0001/sec, ending at a shear rate of 200.01/sec with linear distribution. The duration is 180 sec, 180 data points are collected linear over the measurement. Measurement takes place at shear rates of 40.00, 80.00. 120.00, and 160.00 l/s. The result is reported as the viscosity in mPa·s at a shear rate of 160/s.

Description of the Method for the α-Tocopherol Assay:

The α-tocopherol content is determined by a HPLC method as follows:
Chromatographic System
Column: Lichrospher 100-5 RP8 250*4.0 mm 5 μm or equivalent
Eluent: 10% Trifluor acetic acid 0.3% in water, 90% Trifluor acetic acid 0.3% in acetonitrile
Detection: UV-210 nm
Flow: 1.5 mL/min
Injection volume: 50 μL
Column temperature: 35° C.

Viscosity [mPa · s] @25° C./60% r.h.:

| | | viscosity [mPa · s] | | | |
|---|---|---|---|---|---|
| | content of PEO [%] | start of storage | after 6 months | absolute change over 6 months | decrease over 6 months [%] |
| I 1-1 | 56.29 (Zn containing) | 314 | 273 | −41 | 13 |
| C 1-1 | 56.29 | 390 | 377 | −13 | 3 |
| C 1-2 | (Zn free) | 375 | 305 | −70 | 19 |
| C 1-4 | | 418 | 396 | −22 | 5 |
| I 2-1 | 35.00 | 402 | 361 | −41 | 10 |
| I 2-2 | (Zn containing) | 382 | 289 | −93 | 24 |
| C 2-1 | 35.00 | 464 | 444 | −20 | 4 |
| C 2-2 | (Zn free) | 443 | 405 | −38 | 9 |
| C 2-3 | | 508 | 404 | −104 | 20 |
| C 2-4 | | 506 | 400 | −106 | 21 |

Viscosity [mPa · s] @ 30° C./75% r.h.:

| | | viscosity [mPa · s] | | | | |
|---|---|---|---|---|---|---|
| | content of PEO [%] | start of storage | after 3 months | after 6 months | absolute change over 6 months | decrease over 6 months [%] |
| I 1-1 | 56.29 (Zn containing) | 314 | 317 | 250 | −64 | 20 |
| C 1-1 | 56.29 | 390 | 371 | 344 | −46 | 12 |
| C 1-2 | (Zn free) | 375 | 324 | 301 | −74 | 20 |
| C 1-3 | | 382 | 389 | 358 | −24 | 6 |
| C 1-4 | | 418 | 367 | 333 | −85 | 20 |
| I 2-2 | 35.00 (Zn containing) | 382 | 399 | 357 | −25 | 7 |
| C 2-1 | 35.00 | 464 | 459 | 457 | −7 | 2 |
| C 2-2 | (Zn free) | 443 | 440 | 378 | −65 | 15 |
| C 2-3 | | 508 | 447 | 420 | −88 | 17 |
| C 2-4 | | 506 | 444 | 395 | −111 | 22 |

Viscosity [mPa · s] @ 40° C./75% r.h.:

| | content of PEO [%] | viscosity [mPa · s] start of storage | after 1 month | after 3 months | after 6 months | absolute change over 6 months | decrease over 6 months [%] |
|---|---|---|---|---|---|---|---|
| I 1-1 | 56.29 (Zn containing) | 314 | 344 | 327 | 308 | −6 | 2 |
| I 1-2 | | 272 | 344 | 312 | 254 | −18 | 7 |
| C 1-1 | 56.29 (Zn free) | 390 | 356 | 329 | 282 | −108 | 28 |
| C 1-2 | | 375 | 415 | 304 | 263 | −112 | 30 |
| C 1-3 | | 382 | 343 | 350 | 276 | −106 | 28 |
| C 1-4 | | 418 | 400 | 400 | 270 | −148 | 35 |
| I 2-1 | 35.00 (Zn containing) | 402 | 412 | 405 | 397 | −5 | 1 |
| I 2-2 | | 382 | 396 | 387 | 359 | −23 | 6 |
| C 2-1 | 35.00 (Zn free) | 464 | 477 | 430 | 356 | −108 | 23 |
| C 2-2 | | 443 | 471 | 403 | 342 | −101 | 23 |
| C 2-3 | | 508 | 481 | 411 | 372 | −136 | 27 |
| C 2-4 | | 506 | 449 | 401 | 364 | −142 | 28 |

It becomes evident from the data summarized in above table, that the zinc containing dosage forms according to the invention display improved stability in comparison to dosage forms not containing zinc, in particular at accelerated storage conditions at 40° C. and 75% r.h.

While all inventive examples showed a decrease in viscosity after 6 months of storage (40° C./75% r.h.) of only 1% (I 2-1) up to a maximum decrease of 7% (I 1-2), all comparative examples not containing zinc exhibited a decrease in viscosity of at least 23% (C 2-1 and C 2-2) up to 35% (C 1-4), relative to the respective viscosity at the start of the storage.

In the following, the content of α-tocopherol is given in wt.-% relative to the given theoretical content of α-tocopherol in the pharmaceutical dosage form.

For the purpose of specification, the "given theoretical content of α-tocopherol" shall refer to the weight content the α-tocopherol should have in theory according to the specification of the composition of the pharmaceutical dosage form.

Content (wt.-%) α-tocopherol @25° C./60% r.h.

| | content of PEO [%] | content of α-tocopherol start of storage [wt.-%] | after 6 months [wt.-%] | absolute change over 6 months [wt.-%] | decrease over 6 months [%] |
|---|---|---|---|---|---|
| I 1-1 | 56.29 (Zn containing) | 94 | 90 | −4 | 4 |
| I 1-2 | | 93 | 88 | −5 | 5 |
| C 1-1 | 56.29 (Zn free) | 93 | 87 | −6 | 6 |
| C 1-2 | | 97 | 91 | −6 | 6 |
| C 1-3 | | 94 | 89 | −5 | 5 |
| C 1-4 | | 97 | 90 | −7 | 7 |
| I 2-1 | 35.00 (Zn containing) | 90 | 87 | −3 | 3 |
| I 2-2 | | 89 | 87 | −2 | 2 |
| C 2-1 | 35.00 (Zn free) | 87 | 85 | −2 | 2 |
| C 2-2 | | 93 | 85 | −8 | 9 |
| C 2-3 | | 89 | 87 | −2 | 2 |
| C 2-4 | | 92 | 86 | −6 | 7 |

Content (wt.-%) α-tocopherol @30° C./75% r.h.

| | content of PEO [%] | content of α-tocopherol start of storage [wt.-%] | after 3 months [wt.-%] | after 6 months [wt.-%] | absolute change over 6 months [wt.-%] | decrease over 6 months [%] |
|---|---|---|---|---|---|---|
| I 1-1 | 56.29 (Zn containing) | 94 | 90 | 88 | −6 | 6 |
| I 1-2 | | 93 | 89 | 86 | −7 | 8 |
| C 1-1 | 56.29 (Zn free) | 93 | 89 | 83 | −10 | 11 |
| C 1-2 | | 97 | 91 | 88 | −9 | 9 |
| C 1-3 | | 94 | 92 | 86 | −8 | 9 |
| C 1-4 | | 97 | 93 | 86 | −11 | 11 |
| I 2-1 | 35.00 (Zn containing) | 90 | 88 | 85 | −5 | 6 |
| I 2-2 | | 89 | 88 | 85 | −4 | 4 |
| C 2-1 | 35.00 (Zn free) | 87 | 86 | 81 | −6 | 7 |
| C 2-2 | | 93 | 87 | 80 | −13 | 14 |
| C 2-3 | | 89 | 88 | 83 | −6 | 7 |
| C 2-4 | | 92 | 88 | 82 | −10 | 11 |

Content (wt.-%) α-tocopherol @40° C./75% r.h.

| | content of PEO [%] | content of α-tocopherol start of storage [wt.-%] | after 1 month [wt.-%] | after 3 months [wt.-%] | after 6 months [wt.-%] | absolute change over 6 months [wt.-%] | decrease over 6 months [%] |
|---|---|---|---|---|---|---|---|
| I 1-1 | 56.29 (Zn containing) | 94 | 93 | 86 | 79 | −15 | 16 |
| I 1-2 | | 93 | 93 | 84 | 77 | −16 | 17 |
| C 1-1 | 56.29 (Zn free) | 93 | 89 | 85 | 73 | −20 | 22 |
| C 1-2 | | 97 | 93 | 88 | 78 | −19 | 20 |
| C 1-3 | | 94 | 94 | 89 | 72 | −22 | 23 |
| C 1-4 | | 97 | 93 | 90 | 76 | −21 | 22 |
| I 2-1 | 35.00 (Zn containing) | 90 | 89 | 85 | 76 | −14 | 16 |
| I 2-2 | | 89 | 91 | 84 | 75 | −14 | 16 |
| C 2-1 | 35.00 (Zn free) | 87 | 90 | 85 | 66 | −21 | 24 |
| C 2-2 | | 93 | 91 | 79 | 64 | −29 | 31 |
| C 2-3 | | 89 | 90 | 83 | 71 | −18 | 20 |
| C 2-4 | | 92 | 89 | 82 | 69 | −23 | 25 |

In the data presented it is shown that for the inventive formulations the degradation of the polyethylene oxide is reduced compared to the comparative formulations.

It becomes evident from the data summarized in above table, that the zinc containing dosage forms according to the invention display improved stability in comparison to dosage forms not containing zinc, in particular at accelerated storage conditions at 40° C. and 75% r.h.

While all inventive examples showed a decrease of the α-tocopherol content after 6 months of storage (40° C./75% r.h.) of only 14% (I 1-1) up to a maximum decrease of 17% (I 1-2), all comparative examples not containing zinc exhibited a decrease of the α-tocopherol content of at least 20% (C2-3 and C1-2) up to 31% (C2-2), relative to the respective content of α-tocopherol at the start of the storage.

EXAMPLE 3

The correlation was determined between the breaking strength of the pharmaceutical dosage form and the polyalkylene oxide (irrespective of containing zinc or not).

Mixtures of pharmacologically active ingredient, polyalkylene oxide (not containing zinc) and excipients (Hypromellose and PEG 6000) were extruded by means of a twin-screw-extruder (type ZSE 18 PH 40 D, diameter of extrusion die 9 mm, temperature of extrusion die 120-130° C.).

The composition of the individual mixtures, the respective extrusion conditions and the breaking strengths of the thus obtained dosage forms are summarized in the table here below:

| Ex. | composition ingredient | [wt.-%] | revolution velocity [rpm] | throughput [g/min] | breaking strength [N] |
|---|---|---|---|---|---|
| 1 [5%] | Polyethylene oxide ($M_w$ 5 × 10$^6$) | 5.00 | 120 | 16.66 | 235 |
| | Tramadol HCl | 50.00 | | | |
| | Hypromellose ($M_w$ 1 × 10$^5$) | 30.00 | | | |
| | PEG 6000 | 15.00 | | | |
| 2 [15%] | Polyethylene oxide ($M_w$ 5 × 10$^6$) | 15.00 | 100 | 20 | 785 |
| | Tramadol HCl | 45.00 | | | |
| | Hypromellose ($M_w$ 1 × 10$^5$) | 30.00 | | | |
| | PEG 6000 | 10.00 | | | |
| 3 [35%] | Polyethylene oxide ($M_w$ 5 × 10$^6$) | 35.00 | 100 | 33.33 | >1500 |
| | Tramadol HCl | 45.00 | | | |
| | Hypromellose ($M_w$ 1 × 10$^5$) | 10.00 | | | |
| | PEG 6000 | 10.00 | | | |
| 4 [55%] | Polyethylene oxide ($M_w$ 5 × 10$^6$) | 55.00 | 100 | 33.33 | >1500 |
| | Tramadol HCl | 25.00 | | | |
| | Hypromellose ($M_w$ 1 × 10$^5$) | 10.00 | | | |
| | PEG 6000 | 10.00 | | | |
| 5 [80%] | Polyethylene oxide ($M_w$ 5 × 10$^6$) | 80.00 | 100 | 33.33 | >1500 |
| | Tramadol HCl | 5.00 | | | |
| | Hypromellose ($M_w$ 1 × 10$^5$) | 5.00 | | | |
| | PEG 6000 | 10.00 | | | |
| 6 [55%] | Polyethylene oxide ($M_w$ 7 × 10$^6$) | 55.00 | 100 | 33.33 | >1500 |
| | Tramadol HCl | 24.90 | | | |
| | Hypromellose ($M_w$ 1 × 10$^5$) | 10.00 | | | |
| | PEG 6000 | 10.00 | | | |

The above data demonstrate that under the given experimental conditions high breaking strengths could only be achieved at contents of polyethylene oxide (5×10$^6$ and 7×10$^6$) of 15 wt.-% and above.

The invention claimed is:

1. A thermoformed, tamper-resistant pharmaceutical dosage form comprising:

a) a pharmacologically active ingredient selected from the group consisting of opioids, stimulants, tranquilizers, and narcotics;
   b) a polyalkylene oxide having a weight average molecular weight of more than 200,000 g/mol;
   c) a zinc component, wherein said zinc component has a zinc content of at most 1,000 ppm, relative to a total weight of the dosage form; and
   d) an antioxidant.

2. The pharmaceutical dosage form according to claim 1, wherein the polyalkylene oxide is obtainable by polymerizing alkylene oxide in presence of the zinc component.

3. The pharmaceutical dosage form according to claim 1, wherein an aqueous dispersion of the pure polyalkylene oxide composition in pure water at 25° C. and at a concentration of 1 wt.-% has a pH value of at most 7.7.

4. The pharmaceutical dosage form according to claim 1, wherein the zinc content of said zinc component is at least 10 ppm relative to the total weight of the polyalkylene oxide composition.

5. The pharmaceutical dosage form according to claim 1, which has a breaking strength of at least 300 N.

6. The pharmaceutical dosage form according to claim 1, wherein the pharmacologically active ingredient is an opioid.

7. The pharmaceutical dosage form according to claim 1, wherein the pharmacologically active ingredient is embedded in a controlled-release matrix comprising the polyalkylene oxide and the zinc component.

8. The pharmaceutical dosage form according to claim 1, which is monolithic or multiparticulate.

9. The pharmaceutical dosage form according to claim 1, which is melt-extruded.

10. The pharmaceutical dosage form according to claim 1, which is adapted for administration once daily, twice daily or thrice daily.

11. A process for the manufacture of a pharmaceutical dosage form according to claim 1 comprising the steps of:

(a) mixing the pharmacologically active ingredient, the polyalkylene oxide composition, the zinc component, and the antioxidant, and optionally present excipients to obtain a mixture; and (b) press-forming the mixture obtained in step (a) with preceding, simultaneous, or subsequent exposure to heat.

12. The process according to claim 11, wherein step (b) is performed by means of an extruder.

13. A pharmaceutical dosage form obtainable by the process of claim 12.

14. A method of treating pain in a patient in need thereof, said method comprising administering to said patient a pharmaceutical dosage form according to claim 1, said pharmaceutical dosage form comprising a pharmacologically active ingredient effective to treat pain.

15. A method of reducing the incidence of drug abuse of a pharmacologically active ingredient with abuse potential, said method comprising providing said pharmacologically active ingredient in the form of a pharmaceutical dosage form according to claim 1.

16. The pharmaceutical dosage form according to claim 1, which does not comprise zinc sulfate or zinc stearate.

17. The pharmaceutical dosage form according to claim 1, wherein the content of said zinc component is at least 1 ppm relative to the total weight of the pharmaceutical dosage form.

18. The pharmaceutical dosage from according to claim 1, wherein the antioxidant is selected from the group consisting of butylhydroxytoluene, butylhydroxyanisole and α-tocopherol.

19. The pharmaceutical dosage form according to claim 1, wherein the pharmacologically active ingredient is oxycodone or a physiologically acceptable salt thereof.

20. The pharmaceutical dosage form according to claim 1, wherein the pharmacologically active ingredient is oxymorphone or a physiologically acceptable salt thereof.

21. The pharmaceutical dosage form according to claim 1, wherein the pharmacologically active ingredient is hydrocodone or a physiologically acceptable salt thereof.

22. The pharmaceutical dosage form according to claim 1, wherein the pharmacologically active ingredient is hydromorphone or a physiologically acceptable salt thereof.

23. The pharmaceutical dosage form according to claim 1, wherein the pharmacologically active ingredient is morphine or a physiologically acceptable salt thereof.

24. The pharmaceutical dosage form according to claim 1, wherein the pharmacologically active ingredient is tapentadol or a physiologically acceptable salt thereof.

25. The pharmaceutical dosage form according to claim 1, wherein the pharmacologically active ingredient is amphetamine or a physiologically acceptable salt thereof.

26. The pharmaceutical dosage form according to claim 1, wherein the pharmacologically active ingredient is amphetaminil or a physiologically acceptable salt thereof.

27. The pharmaceutical dosage form according to claim 1, wherein the pharmacologically active ingredient is methamphetamine or a physiologically acceptable salt thereof.

28. The pharmaceutical dosage form according to claim 1, wherein the pharmacologically active ingredient is methylphenidate or a physiologically acceptable salt thereof.

\* \* \* \* \*